(12) United States Patent
Levit

(10) Patent No.: US 11,185,332 B2
(45) Date of Patent: Nov. 30, 2021

(54) MULTI-CHAMBERED BALLOON CATHETER DEVICES AND METHODS

(71) Applicant: RenalPro Medical, Inc., Santa Clara, CA (US)

(72) Inventor: Eran Levit, Amherst, NH (US)

(73) Assignee: RenalPro Medical, Inc., Santa Clara, CA (US)

(*) Notice: Subject to any disclaimer, the term of this patent is extended or adjusted under 35 U.S.C. 154(b) by 100 days.

(21) Appl. No.: 16/447,830

(22) Filed: Jun. 20, 2019

(65) Prior Publication Data
US 2020/0100792 A1 Apr. 2, 2020

Related U.S. Application Data

(60) Provisional application No. 62/688,233, filed on Jun. 21, 2018.

(51) Int. Cl.
*A61B 17/12* (2006.01)
*A61M 25/10* (2013.01)

(52) U.S. Cl.
CPC .... *A61B 17/1204* (2013.01); *A61B 17/12109* (2013.01); *A61B 17/12136* (2013.01); *A61M 25/1002* (2013.01); *A61M 25/1034* (2013.01); *A61M 25/10182* (2013.11); *A61M 2025/1052* (2013.01); *A61M 2025/1072* (2013.01); *A61M 2025/1079* (2013.01); *A61M 2210/1082* (2013.01); *A61M 2210/12* (2013.01)

(58) Field of Classification Search
CPC .... A61M 2025/1072; A61M 2025/107; A61M 2025/1079; A61M 25/1002; A61M 25/1034; A61M 25/10182; A61B 17/12027; A61B 17/12036; A61B 17/1204; A61B 17/12109; A61B 17/12136
See application file for complete search history.

(56) References Cited

U.S. PATENT DOCUMENTS

| | | | |
|---|---|---|---|
| 5,795,331 A * | 8/1998 | Cragg | A61B 17/12022 604/103.01 |
| 5,879,499 A | 3/1999 | Corvi | |
| 6,036,697 A | 3/2000 | DiCaprio | |
| 6,251,093 B1 | 6/2001 | Valley et al. | |
| 6,692,484 B1 | 2/2004 | Karpiel et al. | |
| 6,913,600 B2 | 7/2005 | Valley et al. | |
| 9,861,794 B2 | 1/2018 | Ringvad Andersen et al. | |
| 10,300,252 B2 | 5/2019 | Lee et al. | |
| 10,441,291 B2 | 10/2019 | Koo et al. | |

(Continued)

FOREIGN PATENT DOCUMENTS

| | | |
|---|---|---|
| CN | 201692487 U | 1/2011 |
| WO | WO96/40347 A1 | 12/1996 |
| WO | WO2010/018569 A1 | 2/2010 |

*Primary Examiner* — Tan-Uyen T Ho
*Assistant Examiner* — Bridget E. Rabaglia
(74) *Attorney, Agent, or Firm* — Shay Glenn LLP

(57) ABSTRACT

Catheter devices/systems and methods therefrom are described herein for treating acute kidney injury, especially in the reduction of contrast-induced acute kidney injury. The catheter devices, systems and associated methods may prevent contrast dyes from entering into the kidney and/or facilitate blood flow beyond the kidney by utilization of the catheter devices, systems and associated methods.

37 Claims, 17 Drawing Sheets

(56) References Cited

U.S. PATENT DOCUMENTS

| | | | |
|---|---|---|---|
| 2004/0249342 A1* | 12/2004 | Khosravi | A61M 25/10182 |
| | | | 604/96.01 |
| 2005/0203553 A1 | 9/2005 | Maschke | |
| 2005/0203558 A1 | 9/2005 | Maschke | |
| 2008/0109062 A1 | 5/2008 | Chalekian | |
| 2013/0123621 A1 | 5/2013 | Isham et al. | |
| 2014/0051968 A1 | 2/2014 | Isham et al. | |
| 2014/0222093 A1* | 8/2014 | Mafi | A61B 17/8855 |
| | | | 606/86 R |
| 2016/0375230 A1* | 12/2016 | Lee | A61B 17/1204 |
| | | | 604/509 |
| 2019/0388655 A1 | 12/2019 | Byrne et al. | |

* cited by examiner

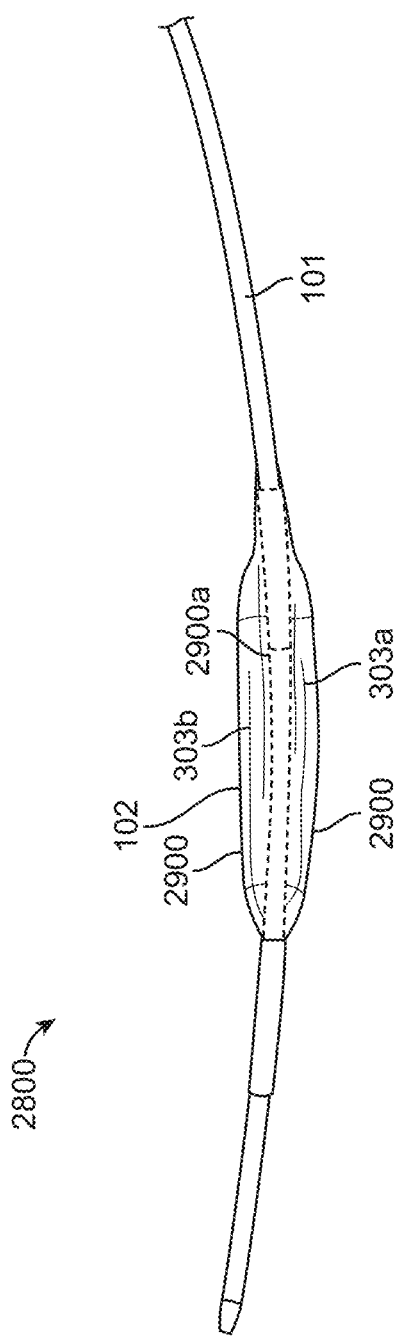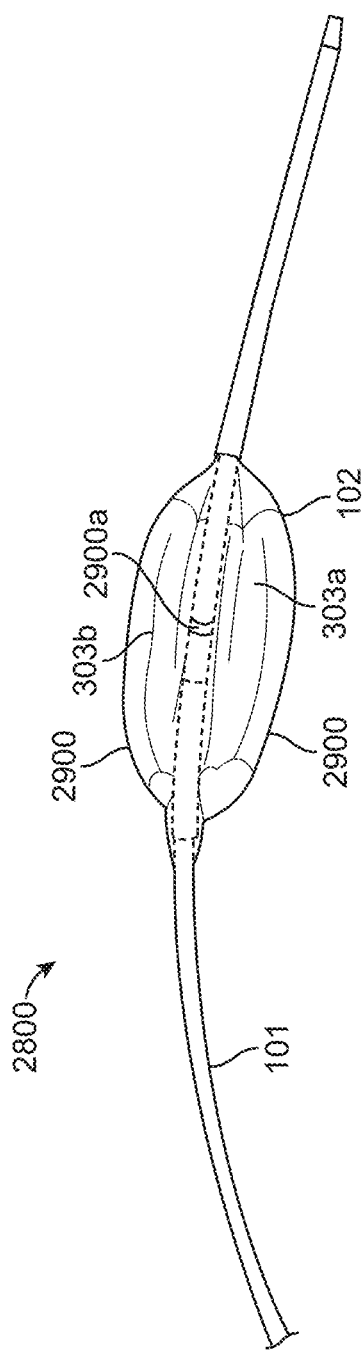
FIG. 7A
FIG. 7B

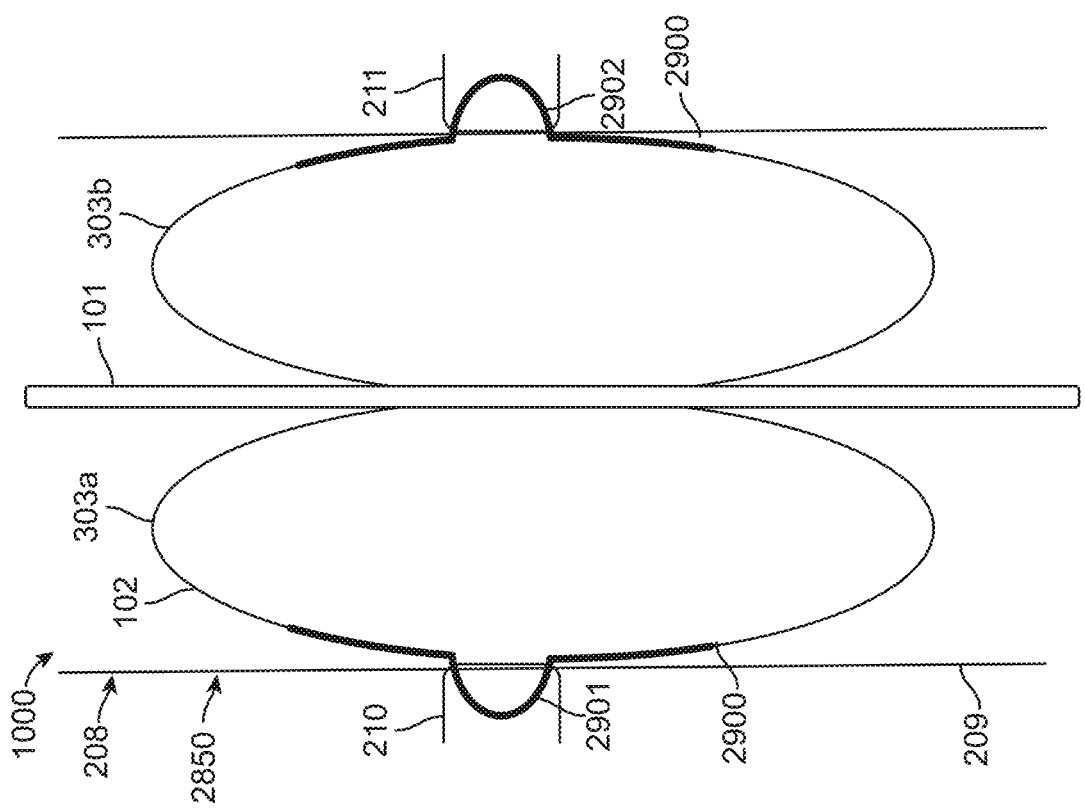
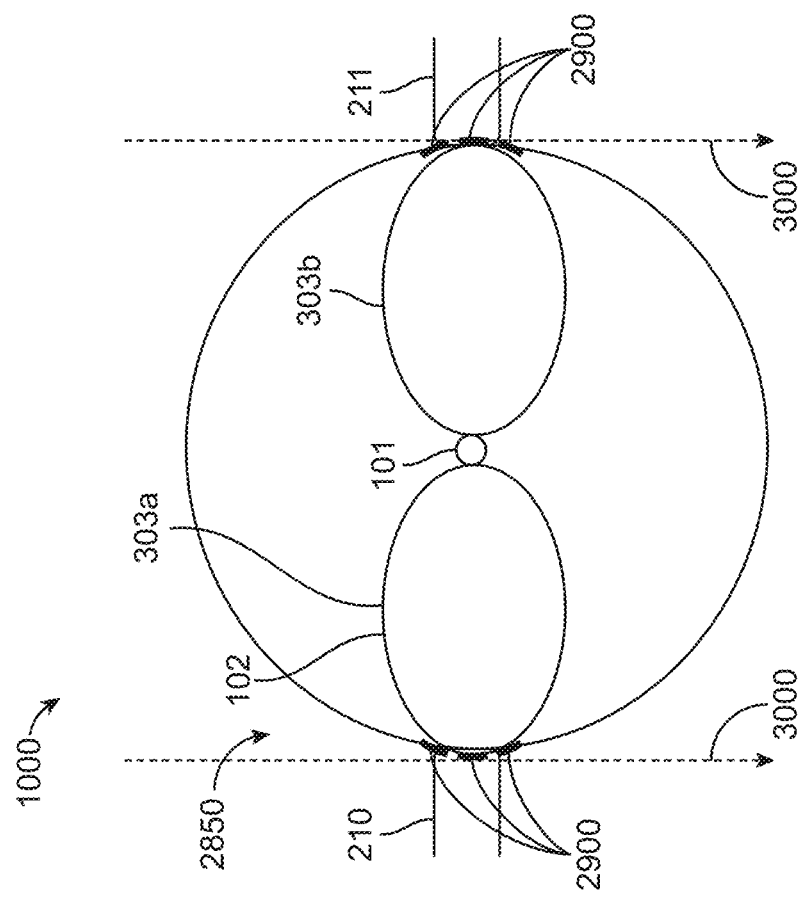
FIG. 11B
FIG. 11A

MULTI-CHAMBERED BALLOON CATHETER DEVICES AND METHODS

CROSS-REFERENCE

This application claims the benefit of U.S. Provisional Application No. 62/688,233, filed Jun. 21, 2018, the entire contents of which are incorporated herein by reference.

The subject matter of the present application is related to the subject matter of U.S. patent application Ser. No. 15/140,502 (filed Apr. 28, 2016), Ser. No. 15/189,460 (filed Jun. 22, 2016), Ser. No. 15/969,050 (filed May 2, 2018), and PCT Application Nos. PCT/US2014/072302 (filed Dec. 23, 2014) and PCT/US2017/031153 (filed May 4, 2017), and U.S. Provisional Application No. 62/688,323 (filed Jun. 21, 2018), the full contents of which are incorporated herein by reference.

BACKGROUND

Acute kidney injury (AKI), also called acute renal failure (ARF), is a rapid loss of kidney function. The causes of AKI are numerous and may include low blood volume, decreased blood flow to the kidneys, exposure of the kidney to toxic substances, or urinary tract obstruction. AKI is diagnosed on the basis of clinical history and laboratory data. Kidney function may be measured by serum creatinine or urine output, among other tests, and a rapid reduction in either or both of these factors may be diagnosed as AKI.

One possible cause of AKI is the use of intravascular iodinated contrast media or contrast agents. Contrast-induced AKI (CI-AKI) is a common problem in patients receiving intravascular iodine-containing contrast media for angiography. CI-AKI is associated with excessive hospitalization cost, morbidity, and mortality. Clinical procedures involving intravascular iodine-containing contrast media injection may include, for example, percutaneous coronary intervention (PCI), peripheral vascular angiography and intervention, transarterial heart valve interventions, and neurological angiography and intervention. In clinical practice, CI-AKI is diagnosed when serum creatinine levels increase by more than either 25% or 0.5 mg/dL above baseline within 48 to 72 hours of exposure to contrast media in the absence of other culprit etiology for AKI.

Management of AKI hinges on identification and treatment of the underlying cause. Additionally, management of AKI routinely includes avoidance of substances toxic to the kidneys, called nephrotoxins. Nephrotoxins include, for example, non-steroidal anti-inflammatory drugs (NSAIDs), such as ibuprofen, iodinated contrast agents, such as those used for CT scans, many antibiotics, such as gentamicin, and a range of other substances.

Renal function monitoring by serum creatinine and urine output is routinely performed. For example, insertion of a urinary catheter helps monitor urine output and relieves possible bladder outlet obstruction, such as with an enlarged prostate. In prerenal AKI without fluid overload, administration of intravenous fluids is typically the first step to improve renal function. Volume status may be monitored with the use of a central venous catheter to avoid over- or under-replacement of fluid. Should low blood pressure prove a persistent problem in the fluid-replete patient, inotropes such as norepinephrine and dobutamine may be given to improve cardiac output and enhance renal perfusion. Also, while a useful pressor, there is no evidence to suggest that dopamine is of any specific benefit, and may in fact be harmful.

The myriad causes of intrinsic AKI can require specific therapies. For example, intrinsic AKI due to Wegener's granulomatosis may respond to steroid medication while toxin-induced prerenal AKI often responds to discontinuation of the offending agent, which may, for example, be aminoglycoside, penicillin, NSAIDs, or paracetamol. Obstruction of the urinary tract may also cause AKI and treatment may require relief of the obstruction, for example with a nephrostomy or urinary catheter.

Renal replacement therapy, such as with hemodialysis, may be instituted in some cases of AKI. A systematic review of the literature in 2008 shows no difference in outcomes between the use of intermittent hemodialysis and continuous venovenous hemofiltration (CVVH). Among critically ill patients, intensive renal replacement therapy with CVVH does not appear to improve outcomes compared to less intensive intermittent hemodialysis.

Current prevention strategies for AKI, particularly for CI-AKI, are mainly supportive. They include, for example, (1) evaluating and stratifying patients with Mehran risk score before performing PCI, (2) avoiding high-osmolar contrast media by using low-osmolar or iso-osmolar contrast media, (3) reducing the amount of contrast media during PCI, (4) applying intravenously isotonic sodium chloride solution or sodium bicarbonate solution hours before and after PCI, and (5) avoiding use of nephrotoxic drugs (such as nonsteroidal anti-inflammatory drugs, aminoglycosides antibiotics, etc.). (See Stevens 1999, Schweiger 2007, Solomon 2010.) However, none of these strategies have proven to be consistently effective in preventing CI-AKI.

References relevant to the present disclosure may include: U.S. Pat. No. 5,879,499, WO1996040347, WO2010018569, U.S. Pat. No. 6,913,600, U.S. Pat. No. 6,251,093, US20050148997, U.S. Pat. No. 9,861,794, WO2015100393, CN201692487, U.S. Pat. No. 6,692,484, U.S. Pat. No. 6,036,697, US20130123621, US20050203553, US2005203558, and US20140051968.

SUMMARY

Aspects of the present disclosure provide devices for occluding vasculature of a subject. An exemplary device may comprise a catheter shaft and an inflatable balloon. The catheter shaft may comprise a proximal portion and a distal portion. The inflatable balloon may be disposed on the proximal portion of the catheter shaft. The inflatable balloon may comprise a first balloon chamber and a second balloon chamber. The first and second balloon chambers may be formed by one or more of (i) fixedly attaching a first length of the inflatable balloon to the catheter shaft along a longitudinal axis of the catheter to form a first longitudinal bond extending thereon or (ii) fixedly attaching a second length of the inflatable balloon to the catheter shaft along the longitudinal axis of the catheter to form a second longitudinal bond extending thereon. The inflatable balloon may have an expanded configuration which, when advanced into a blood vessel and positioned adjacent blood vessel ostia of the subject, may be sized to occlude the blood vessel ostia while allowing blood flow over the catheter shaft. The distal portion may be configured to remain outside a body of the subject when the proximal portion is positioned adjacent blood vessel ostia of the subject.

The first balloon chamber may be disposed on a first lateral side of the proximal portion and the second balloon chamber may be disposed on a second lateral side of the proximal portion. The first balloon chamber and second balloon chamber may each be longitudinal cylindrical balloon chambers. The first balloon chamber and the second balloon chamber may be in fluid communication with one another. The first balloon chamber and the second balloon chamber may be configured to inflate simultaneously. The first longitudinal bond fixedly attaching the inflatable balloon to the catheter shaft may extend 80% of the length of the inflatable balloon. The second longitudinal bond may extend 90% of the length of the inflatable balloon. The inflatable balloon may comprise a figure-eight, dumbbell, or butterfly-like cross section about the catheter shaft disposed therein.

The device may further comprise one or more position indication features disposed on the expandable balloon. The one or more position indication feature may comprise one or more radio-opaque markers, which may comprise one or more radio-opaque longitudinal marker. The one or more radio-opaque longitudinal markers may comprise a plurality of radio-opaque longitudinal markers disposed on the expandable balloon along a longitudinal axis of the expandable balloon. The one or more radio-opaque longitudinal markers may be configured to indicate the orientation of the expandable balloon when positioned adjacent renal artery ostia of the subject. The one or more radio-opaque longitudinal markers may be configured to change from a straight configuration to a bowed configuration when expanded adjacent blood vessel ostia of the subject.

The first and/or second lengths of the inflatable balloon may be fixedly attached to the catheter shaft by adhering or bonding the inflatable balloon to the catheter shaft, such as with an adhesive or thermal bond.

The device may be configured for preventing acute kidney injury from contract agent introduced into vasculature of the subject. The blood vessel may be an abdominal aorta and the blood vessel ostia may be renal artery ostia.

Aspects of the present disclosure also provide systems for occluding vasculature of a subject. An exemplary system may comprise a catheter shaft, an inflatable balloon, and a time-delayed release mechanism. The catheter shaft may comprise proximal portion and a distal portion. The inflatable balloon may be disposed on the proximal portion or the catheter shaft. The time-delayed release mechanism may be in communication with the inflatable balloon. The inflatable balloon may comprise a first balloon chamber and a second balloon chamber. The first and second balloon chambers may be formed by one or more of (i) fixedly attaching a first length of the inflatable balloon to the catheter shaft along a longitudinal axis of the catheter to form a first longitudinal bond extending thereon or (ii) fixedly attaching a second length of the inflatable balloon to the catheter shaft along the longitudinal axis of the catheter to form a second longitudinal bond extending thereon. The inflatable balloon may have an expanded configuration which, when advanced into a blood vessel and positioned adjacent blood vessel ostia of the subject, may be sized to occlude the blood vessel ostia while allowing blood flow over the catheter shaft. The distal portion may be configured to remain outside a body of the subject when the proximal portion is positioned adjacent blood vessel ostia of the subject. The time-delayed release mechanism may be configured to collapse the inflatable balloon after a pre-determined amount of time following expansion of the inflatable balloon.

The first balloon chamber and second balloon chamber may each be longitudinal cylindrical balloon chambers. The first balloon chamber and the second balloon chamber may be in fluid communication with one another. The first balloon chamber and the second balloon chamber may be configured to inflate simultaneously. The first longitudinal bond may extend 80% of the length of the inflatable balloon. The second longitudinal bond may extend 90% of the length of the inflatable balloon. The inflatable balloon may comprise a figure-eight, dumbbell, or butterfly-like cross section about the catheter shaft disposed therein.

The time-delayed release mechanism may comprise an energy accumulation and storage component. The energy accumulation and storage component may comprise a spring. The energy accumulation and storage component may comprise a syringe comprising a plunger, and wherein the spring is coupled to the plunger.

The system may further comprise one or more position indication features disposed on the expandable balloon. The one or more position indication feature may comprise one or more radio-opaque markers, which may comprise one or more radio-opaque longitudinal marker. The one or more radio-opaque longitudinal markers may comprise a plurality of radio-opaque longitudinal markers disposed on the expandable balloon along a longitudinal axis of the expandable balloon. The one or more radio-opaque longitudinal markers may be configured to indicate the orientation of the expandable balloon when positioned adjacent renal artery ostia of the subject. The one or more radio-opaque longitudinal markers may be configured to change from a straight configuration to a bowed configuration when expanded adjacent blood vessel ostia of the subject.

The first and/or second lengths of the inflatable balloon may be fixedly attached to the catheter shaft by adhering or bonding the inflatable balloon to the catheter shaft, such as with an adhesive or thermal bond.

The system may be configured for preventing acute kidney injury from contract agent introduced into vasculature of the subject. The blood vessel may be an abdominal aorta and the blood vessel ostia may be renal artery ostia.

Aspects of the present disclosure also provide methods of preventing acute kidney injury from contract agent introduced into vasculature of a subject. In an exemplary method, a proximal portion of a catheter device comprising a catheter shaft and an inflatable balloon may be positioned in an abdominal aorta of the subject adjacent renal artery ostia of the subject. The inflatable balloon may comprise a first balloon chamber and a second balloon chamber. The first and second balloon chambers may be formed by one or more of (i) fixedly attaching a first length of the inflatable balloon to the catheter shaft along a longitudinal axis of the catheter to form a first longitudinal bond extending thereon or (ii) fixedly attaching a second length of the inflatable balloon to the catheter shaft along the longitudinal axis of the catheter to form a second longitudinal bond extending thereon. The first and second balloon chambers of the inflatable balloon of the catheter device may be inflated to occlude the renal artery ostia. A bolus of the contrast agent may be introduced into the abdominal aorta of the subject while the inflatable balloon may be inflated to occlude the renal artery ostia, thereby preventing the contrast agent from entering into renal arteries of the subject. The first and second balloon chambers of the inflatable balloon may be deflated after the bolus of the contrast agent has been introduced, thereby allowing blood flow to the renal arteries to resume.

One or more position indication feature may be disposed on the inflatable balloon. The proximal portion of the catheter device may be positioned by observing one or more of a position or orientation of the one or more position indication features and positioning the proximal portion of the catheter device in response to the observed position or orientation. The one or more position indication features may comprise one or more radio-opaque markers, which may be observed via x-ray imaging. The one or more radio-opaque longitudinal markers may be configured to change from a straight configuration to a bowed configuration when expanded adjacent blood vessel ostia of the subject. Occlusion of the renal artery ostia may be confirmed when the inflatable balloon is inflated. Wherein the one or more position indication features comprise one or more radio-opaque longitudinal markers, the occlusion of the renal artery ostia may be confirmed by observing the appearance of a bowed section in the one or more radio-opaque longitudinal markers using x-ray imaging.

The first balloon chamber and second balloon chamber may each be longitudinal cylindrical balloon chambers. The first balloon chamber and the second balloon chamber may be in fluid communication with one another. The first and second balloon chambers may be inflated simultaneously. The first and second balloon chambers may be deflated after a pre-determined amount of time. The inflation of the first and second balloon chambers and the introduction of the bolus of the contrast agent may be synchronized.

The first and/or second lengths of the inflatable balloon may be fixedly attached to the catheter shaft by adhering or bonding the inflatable balloon to the catheter shaft, such as with an adhesive or thermal bond.

Aspects of the present disclosure also provide methods of manufacturing devices for occluding vasculature of a subject. In an exemplary method, a balloon catheter device comprising (i) a catheter shaft comprising a proximal portion and a distal portion and (ii) an inflatable balloon comprising a distal end and a proximal end and disposed on the proximal portion of the catheter shaft may be provided. The inflatable balloon may be fixedly attached to the catheter shaft at distal and proximal ends of the inflatable balloon to form fluid-tight seals. A first length of the inflatable balloon may be fixedly attached to the catheter shaft along a longitudinal axis of the catheter to form a first longitudinal bond extending thereon.

The inflatable balloon may comprise a cylindrical balloon.

Bonding of the first length of the inflatable balloon may deform the inflatable balloon such that the inflatable balloon has a heart-shaped cross-section about the catheter shaft.

The first longitudinal bond may extend at least 80% of the length of the inflatable balloon.

A second length of the inflatable balloon may be bonded to the catheter shaft along the longitudinal axis of the catheter shaft to form a second longitudinal body extending thereon. The bonding of the second length of the inflatable balloon may split the inflatable balloon into a first balloon chamber and a second balloon chamber. The first balloon chamber may be disposed on a first lateral side of the proximal portion, and the second balloon chamber may be disposed on a second lateral side of the proximal portion. The inflatable balloon may comprise a cylindrical balloon, and the first balloon chamber and second balloon chamber may each comprise longitudinal cylindrical balloon chambers. The first balloon chamber and the second balloon chamber may be in fluid communication with one another. The second longitudinal bond may extend at least 80% of the length of the inflatable balloon.

The inflatable balloon may have an expanded configuration which, when advanced into a blood vessel and positioned adjacent blood vessel ostia of the subject, may be sized to occlude the blood vessel ostia while allowing blood flow over the catheter shaft. The blood vessel may be an abdominal aorta, and the blood vessel ostia may be renal artery ostia.

The first length of the inflatable balloon may be fixedly attached to the catheter shaft by one or more of adhering or bonding the first length of the inflatable balloon to the catheter shaft, such as with an adhesive or thermal bond. Likewise, the second length of the inflatable balloon may be fixedly attached to the catheter shaft by one or more of adhering or bonding the second length of the inflatable balloon to the catheter shaft, such as with an adhesive or thermal bond.

The balloon catheter device may be provided by providing the catheter shaft comprising the proximal portion and the distal portion, providing the inflatable balloon comprising the proximal end and the distal end, disposing the inflatable balloon on the proximal portion of the catheter shaft, fixedly attaching the distal end of the inflatable balloon to the catheter shaft to form a fluid-tight seal, and fixedly attaching the proximal end of the inflatable balloon to the catheter shaft to form a fluid-tight seal.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

FIG. 3A shows a side view of a cylinder-like inflated balloon. FIG. 3B shows a cross-section view of the cylinder-like inflated balloon of FIG. 3A. FIG. 3C shows a side view of the morphology of an exemplary inflated balloon which is "butterfly-like". FIG. 3D shows a cross-section view of the butterfly-like inflated balloon of FIG. 3C. FIG. 3E shows a side view of an elongated butterfly-like balloon with two ellipsoidal balloon chambers formed from a cylinder-like balloon. FIG. 3F shows a cross-section view of the elongated butterfly-like balloon of FIG. 3E.

FIG. 4A shows a cross-section of a cylinder-like balloon disposed about a catheter shaft (shown in the inflated configuration). FIG. 4B shows the balloon after a first length of the inflatable balloon has been fixedly attached to the catheter shaft along a longitudinal axis of the catheter to form a first longitudinal bond extending thereon and generate a balloon having a heart-shaped cross-section about the catheter. FIG. 4C shows the balloon after a second length of the inflatable balloon has been fixedly attached to the catheter shaft along the longitudinal axis of the catheter to form a second longitudinal bond extending thereon and generate a balloon having a butterfly-like or figure-eight shaped cross-section about the catheter.

FIG. 5A shows a perspective view of the balloon of FIG. 4A. FIG. 5B shows a cross-section of the balloon of FIG. 5A. FIG. 5C shows a perspective view of the balloon of FIG. 4C. FIG. 5D shows a cross-section of the balloon of FIG. 5C.

FIG. 6A shows a top view of the device. FIGS. 6B and 6C show perspective views of the device from different angles. FIG. 6D shows a bottom view of the device.

FIGS. 7A-7C show a top views of another balloon catheter device, according to many embodiments. FIG. 7A shows a balloon catheter device having two ellipsoidal balloon chambers, one balloon chamber for occluding each of the left and right renal arteries, in a collapsed configuration. FIG. 7B shows the balloon catheter in an expanded configuration. FIG. 7C shows the balloon catheter in the expanded configuration inside a model abdominal aorta.

FIGS. 8A and 8B shows an axial view along the abdominal aorta depicting the relative positions of the left and right balloon chambers in the initial position (FIG. 8A) and the "protective" or expanded position (FIG. 8B). FIGS. 8C and 8D show the position indication feature in the initial position (FIG. 8C) and the "protected" or expanded position (FIG. 8D).

FIG. 10A shows a perspective view of a balloon with a butterfly-like or figure-eight shaped cross-section about the catheter and having a plurality of longitudinal position indication features extending thereon. FIG. 10B shows a cross-section perspective view of the balloon of FIG. 10A. FIG. 10C shows a side view of the device.

FIGS. 11A-11B show the deployment of the balloon catheter of FIGS. 10A-10C, with the balloon chambers in the "protective" position inside the aorta, according to many embodiments. FIG. 11A shows a cross-section view of the balloon catheter device of FIGS. 10A-10C deployed in an aorta, with the balloon chambers in the "protective" position. FIG. 11B shows a lateral view of the balloon catheter device of FIGS. 10A-10C deployed in an aorta, with the balloon chambers in the "protective" position.

FIG. 13A shows a cross-section view of the balloon catheter device of FIGS. 10A-10C deployed in an aorta, with the balloon chambers malpositioned. FIG. 13B shows a lateral view of the balloon catheter device of FIGS. 10A-10C deployed in an aorta, with the balloon chambers malpositioned.

DETAILED DESCRIPTION

While various embodiments of the present disclosure have been shown and described herein, it will be obvious to those skilled in the art that such embodiments are provided by way of example only. Numerous variations, changes, and substitutions may occur to those skilled in the art without departing from the scope of the present disclosure. It should be understood that various alternatives to the embodiments of the present disclosure may be employed.

Provided herein are devices and systems that specifically focus on solving one or both of the two main pathophysiological culprits of CI-AKI—prolonged transit of contrast media inside the kidneys and renal outer medulla ischemia. In some embodiments, devices, systems, and methods are provided for reducing contrast media concentrations or amounts entering the renal arteries to prevent AKI, for example, CI-AKI. Alternatively or in combination, some embodiments provide devices, systems, and methods for augmenting blood flow towards the renal arteries that feed the kidneys to treat or prevent renal ischemia.

In many embodiments, the device may comprise an occlusive element. The occlusive element may comprise any of the balloons, membranes, or expandable elements (e.g., mesh braid) described herein, in PCT/US2014/072302, and/or in PCT/US2017/031153. The occlusive element may, for example, be an inflatable balloon having at least two balloon chambers as described herein. The occlusive element may be disposed on or around a proximal portion of a catheter. The occlusive element may be advanced into an abdominal aorta and positioned adjacent renal ostia in a collapsed configuration. The occlusive element may then be expanded (e.g., inflated) into an expanded configuration which is sized to partially or fully occlude or divert blood flow from the renal artery ostia while allowing blood flow over the catheter shaft. It will be understood by one of ordinary skill in the art that any of the occlusive elements (e.g., balloons, membranes, braids, etc.) described herein or any of the features thereof may be combined as desired in order to arrive at a device for treating or preventing AKI. Any of the occlusive elements, or any combination thereof, may be combined with any of the position indication means or features, flow disturbing means or elements, flow pumps, sensors, flow augmentation means or elements, injection synchronizer, fluid balancer, time-delayed release mechanism, any other element described herein, in PCT/US2014/072302, and/or in PCT/US2017/031153, or any combination thereof, as desired by one of ordinary skill in the art, to arrive at a device for treating or preventing AKI.

Figure 1:
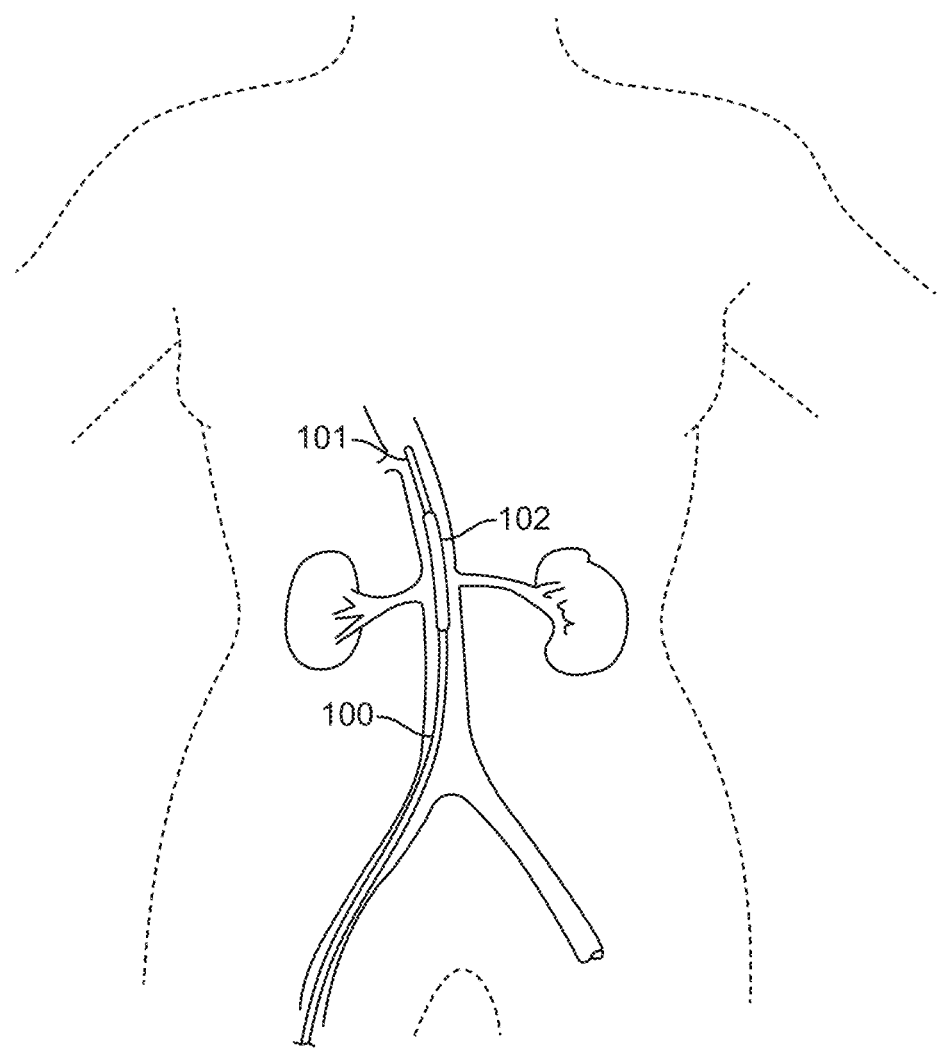
FIG. 1 illustrates a device comprising a balloon catheter having an inflatable balloon positioned in the supra-renal aorta near the orifices of the bilateral renal arteries for treating AKI, according to many embodiments.

FIG. 1 shows a device for occluding vasculature of a subject, for example, for treating or preventing AKI, for example, CI-AKI, comprising a balloon catheter device. The device 100 may comprise a catheter 101 and an inflatable balloon 102. The device 100 optionally may comprise a position indication means, for example, a radio-opaque marker, on the tip of the catheter 101 or disposed on the inflatable balloon 102 as described herein. The device 100 may be inserted into a blood vessel, for example, the abdominal aorta, of a patient and optionally positioned by monitoring the position of the radio-opaque marker for guidance. The device 100 may be inserted into the abdominal aorta using either a trans-femoral arterial approach, a trans-brachial artery approach, or a trans-radial artery approach. The tip of the catheter 101, which may or may not include a radio-opaque marker, may be situated so as to position the inflatable balloon 102 in the blood vessel, for example, the supra-renal aorta, such that the inflatable balloon lies near the orifice(s) of the blood vessel, for example, the orifices of bilateral renal arteries.

The position indication means may, for example, be a radio-opaque marker, or other detectable marker, in order to improve visibility of the device during deployment, for example, with fluoroscopy or radiography.

The position indication means may, for example, be a radio-opaque marker. One or more position indication means may be located on the tip of the catheter 101, on the inflatable balloon 102, or any combination thereof. The position indication means may be used to monitor the position of the device 100 upon insertion, during use, and/or during removal. The device 100 may be inserted into the abdominal aorta, for example, by using either a trans-femoral arterial approach, a trans-brachial artery approach, or a trans-radial artery approach.

Figure 2:
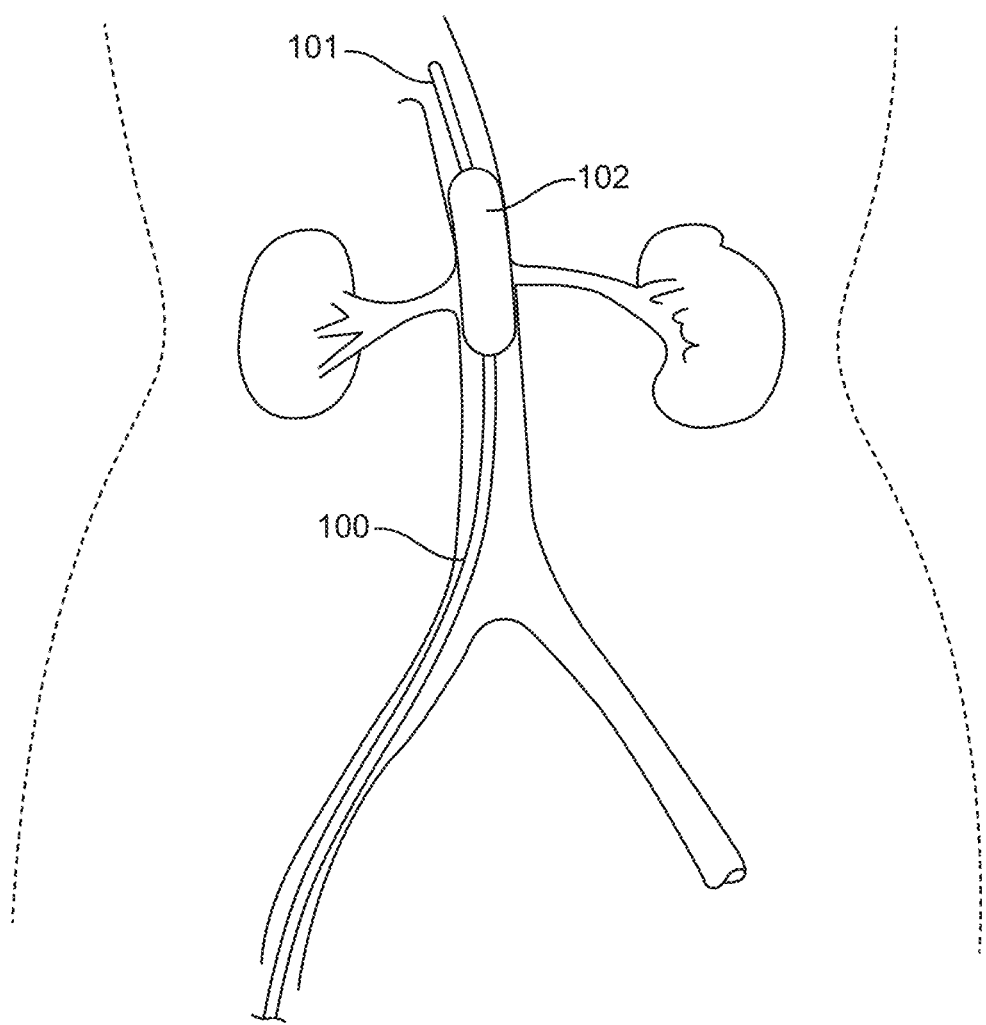
FIG. 2 shows the device illustrated in FIG. 1, wherein the inflatable balloon is inflated to occlude the orifices of both sides of the renal arteries, according to many embodiments.

FIG. 2 shows the device 100 positioned in the supra-renal aorta near the orifices of the bilateral renal arteries. The inflatable balloon 102 may be inflated such that the balloon 102 occludes the orifices of both sides of the renal arteries. Occlusion of the renal arteries by the first balloon 102 may prevent a bolus influx of harmful agents, for example, a contrast media, from flowing into the renal arteries from the supra-renal aorta. Such occlusion may reduce the toxic effects of said harmful agents by preventing delivery of the harmful agents to the kidney. The bolus of contrast media may be introduced using the same device 100 or a separate device that has been introduced either through the same or different path in the vasculature.

In some embodiments, the balloon may be fully inflated such that its outer circumference contacts the aorta wall, heretofore defined as 100% inflation. In some embodiments, the balloon may be inflated to 90%, 80%, 70%, 60%, 50%, 40%, or 30% of full inflation. The balloon may alternatively or in combination be inflated within a range from about 99.9% to about 10%, within a range from about 80% to about 20%, or within a range from about 70% to about 30%.

Figure 3A:
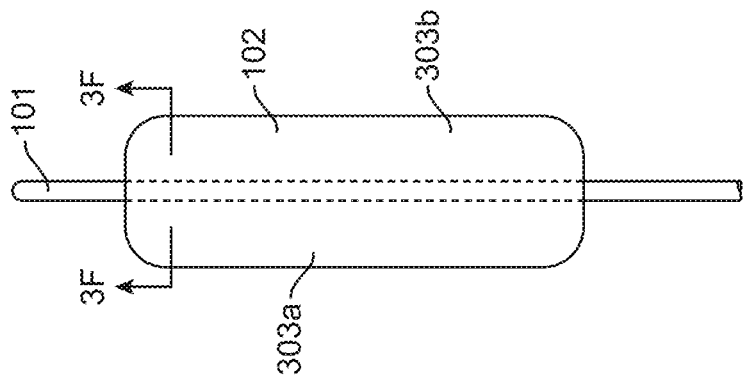
FIGS. 3A-3F show various inflatable balloons suitable for use with the device of FIG. 1, according to many embodiments.
Figure 3B:
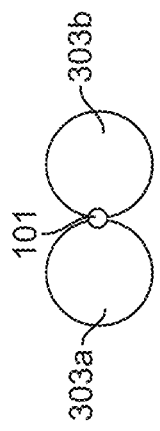
Figure 3C:
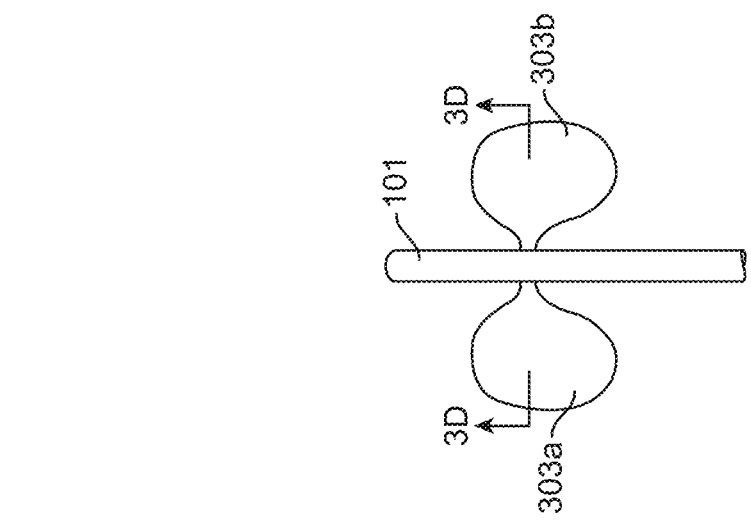
Figure 3D:
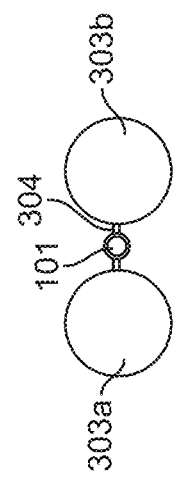
Figure 3E:
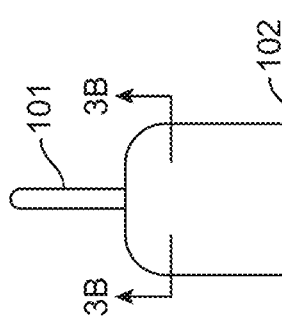
Figure 3F:
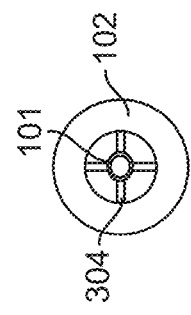

FIGS. 3A to 3D illustrate various embodiments of the inflatable balloon 102. FIG. 3A shows an inflated balloon 102 positioned along and circulating the catheter 101. FIG. 3B shows a cross-sectional view of the inflatable balloon 102 of FIG. 3A. The balloon may be positioned around the catheter 101 such that a hollow area is formed between the inner edge of the balloon 102 and the catheter 101 to form a donut-like balloon shape. By providing a hollow space inside of the balloon 102, blood may be allowed to flow along the catheter 101 when the balloon 102 is inflated to occlude the orifices of both sides of the renal arteries. The balloon 102 may be inflated via at least one connection tube 304 extending from the catheter 101 to the balloon 102. For example, the balloon may be inflated via four connection tubes 304 as shown in FIG. 3B. FIG. 3C shows an alternative embodiment of the inflatable balloon 102. The balloon 102 may be comprised of bilateral inflated balloon sections (also referred to herein as chambers) 303a and 303b to form a butterfly-like balloon shape. The sections 303a and 303b may be connected to each side of catheter 101 via at least one connection tube 304. Inflation of the balloon sections 303a and 303b may occlude the orifices of both sides of the renal arteries while also allowing blood to flow along the catheter 101. FIG. 3D shows a cross-sectional view of the butterfly-like embodiment of the first balloon 102 depicted in FIG. 3C. The balloon sections 303a and 303b may be connected to the catheter 101 via one or more connection tube 304. For example, FIG. 3D depicts one connection tube per balloon section on each side of the catheter 101. In some embodiments, the balloon may have one, two, three, four, five, or more connection tubes 304 to connect the first balloon 102 to the catheter 101. The connection tube(s) may be used to provide inflation or deflation of the first balloon 102. FIGS. 3E-3F show another embodiment of the inflatable balloon 102. FIG. 3E shows a side view of an elongated butterfly-like balloon 102 with two ellipsoidal balloon chambers 303a, 303b formed from a cylinder-like balloon (as shown is FIGS. 4A-5D). The balloon 102 may be fixedly attached to the catheter shaft 101 disposed coaxially therein so as to form at least two bilateral inflated balloon chambers 303a and 303b to form an axially elongated butterfly-like balloon shape. The chambers 303a and 303b may be attached (e.g., bonded) to catheter 101 along at least one length of the inflatable balloon 102 along a longitudinal axis of the catheter 101. Inflation of the balloon chambers 303a and 303b may occlude the orifices of both sides of the renal arteries while also allowing blood to flow along the catheter 101. FIG. 3F shows a cross-section view of the elongated butterfly-like balloon of FIG. 3E. The balloon chambers 303a and 303b may be coupled to the catheter 101 via one or more longitudinal bonds as described herein. For example, FIG. 3F depicts two bonds to the catheter to form the two chambers 303a, 303b on each side of the catheter 101.

In some embodiments, the inflatable balloon 102 may have a toroidal or donut-like shape after inflation. In some embodiments, the inflatable balloon 102 may have a butterfly-like, figure-eight, or dumbbell cross-sectional shape about the catheter shaft 101 disposed therein after inflation.

In some embodiments, the catheter shaft may comprise a fluid outlet port disposed within the balloon 102. The fluid outlet port may be in fluid communication with a source of inflation fluid (e.g., $CO_2$). The fluid outlet port may be used to provide inflation or deflation of the first balloon 102.

Figure 4C:
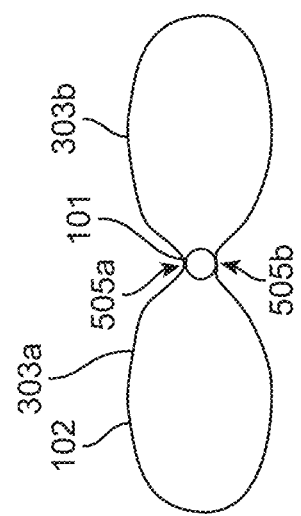
FIGS. 4A-4C show device cross-sections during an exemplary method of manufacturing an inflatable balloon having two balloon chambers, according to many embodiments.
Figure 4B:
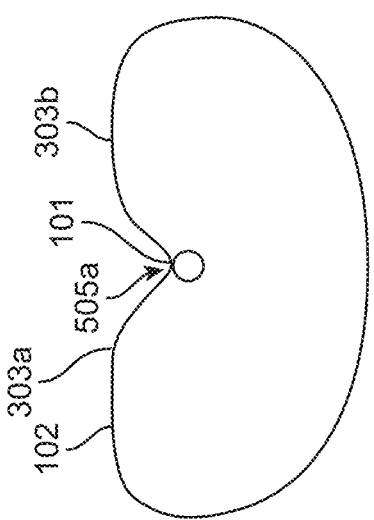
Figure 4A:
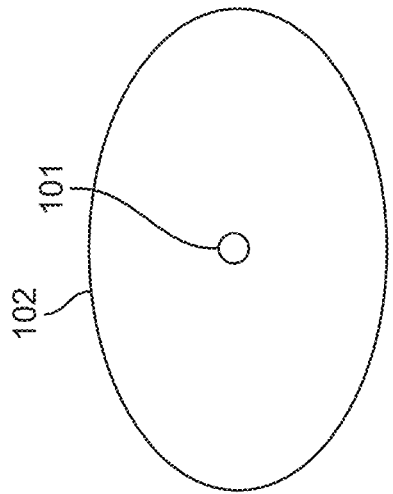

FIGS. 4A-4C show a method of manufacturing an inflatable balloon 102 having two balloon chambers 303a, 303b. FIG. 4A shows a cross-section of a cylinder-like balloon (shown in the inflated configuration for clarity) disposed about a catheter shaft 101. In some embodiments, an inflatable balloon (e.g., an elongate tube or tunnel membrane) 102 may be disposed about the catheter shaft 101 and bonded at its distal and proximal ends to the catheter shaft to form fluid tight seals and generate a cylinder-like balloon as shown in FIG. 4A. In some embodiments, the inflatable balloon 102 may be a standard cylindrical or barrel balloon catheter. FIG. 4B shows the balloon 102 after a first length of the inflatable balloon 102 has been fixedly attached to the catheter shaft 101 along a longitudinal axis of the catheter 101 to form a first longitudinal bond 505a extending thereon and generate a balloon having a heart-shaped cross-section about the catheter with balloon chambers 303a and 303b. In some embodiments, the balloon 102 with the heart-shaped cross-section may, for example, be deployed in a blood vessel as described herein. In some instances, one or more additional bonds may be formed to generate balloon chambers as described herein. FIG. 4C shows the balloon 102 after a second length of the inflatable balloon has been fixedly attached to the catheter shaft 101 along the longitudinal axis of the catheter 101 to form a second longitudinal bond 505b extending thereon, generating a balloon 102 having a butterfly-like or figure-eight shaped cross-section about the catheter with balloon chambers 303a and 303b. Additional bonds may be formed using the methods described herein as desired by one of ordinary skill in the art.

In some embodiments, the inflatable balloon 102 may comprise a first balloon chamber 303a and a second balloon chamber 303b. The first balloon chamber 303a may be disposed on a first lateral side of the proximal portion of the catheter 101. The second balloon chamber 303b may be disposed on a second lateral side of the proximal portion of the catheter 101.

In some embodiments, the first balloon chamber 303a and second balloon chamber 303b may each longitudinal cylindrical balloon chambers.

In some embodiments, the inflatable balloon 102 may comprise one balloon chamber. In some embodiments, the inflatable balloon 102 may comprise at least two balloon chambers formed from a single balloon body as shown in FIG. 4C. The inflatable balloon 102 may comprise a plurality of balloon chambers, for example, 3, 4, 5, 6, 7, 8, 9, 10, 11, 12, 13, 14, 15, 16, 17, 18, 19, or 20 chambers. It will be apparent to one of ordinary skill in the art that any number of chambers may be formed using the methods described herein as desired for a particular use or medical procedure.

In some embodiments, the one or more balloon chambers are formed by attaching the inflatable balloon to the catheter disposed coaxially therein along one or more lengths of the inflatable balloon along the longitudinal axis of the catheter to form one or more longitudinal bonds extending thereon. The inflatable balloon 102 may, for example, be attached to the catheter with one longitudinal bond. The inflatable balloon 102 may, for example, be attached to the catheter with a plurality of longitudinal bonds, for example, 2, 3, 3, 4, 5, 6, 7, 8, 9, 10, 11, 12, 13, 14, 15, 16, 17, 18, 19, or 20 longitudinal bonds.

In some embodiments, the one or more balloon chambers are formed by removably attaching the inflatable balloon to the catheter disposed coaxially therein.

In some embodiments, the one or more balloon chambers are formed by fixedly attaching the inflatable balloon to the catheter disposed coaxially therein. In some embodiments, the one or more balloon chambers are formed by adhering the inflatable balloon to the catheter disposed coaxially therein. In some embodiments, the one or more balloon chambers are formed by bonding the inflatable balloon to the catheter disposed coaxially therein.

In some embodiments, the one or more balloon chambers are formed by bonding the inflatable balloon to the catheter disposed coaxially therein. The one or more balloon chambers may be formed by bonding the inflatable balloon to the catheter using one or more of the following methods: RF welding, adhesive bonding, thermal bonding, and the like.

Figure 5A:
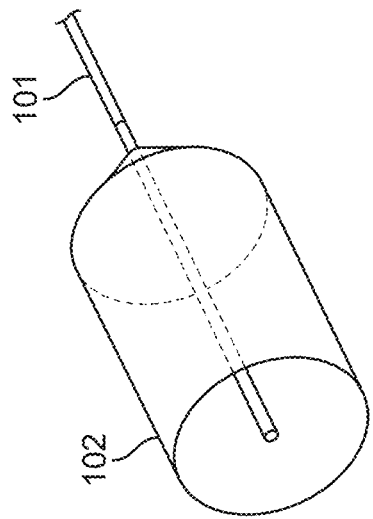
FIGS. 5A-5D show perspective views of the inflatable balloon of FIGS. 4A and 4C.
Figure 5B:
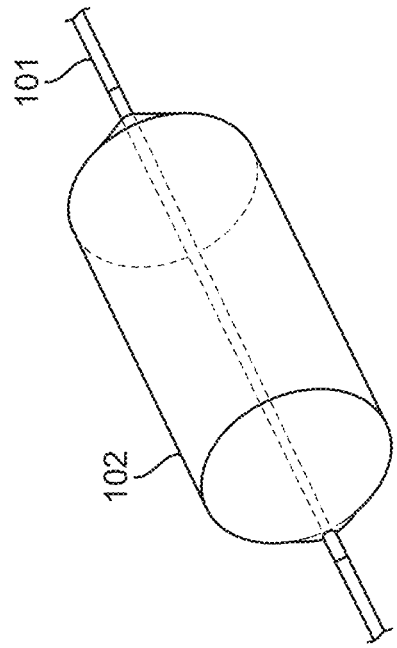
Figure 5C:
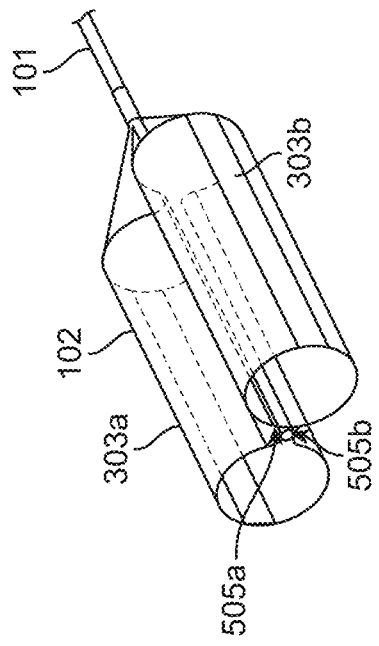
Figure 5D:
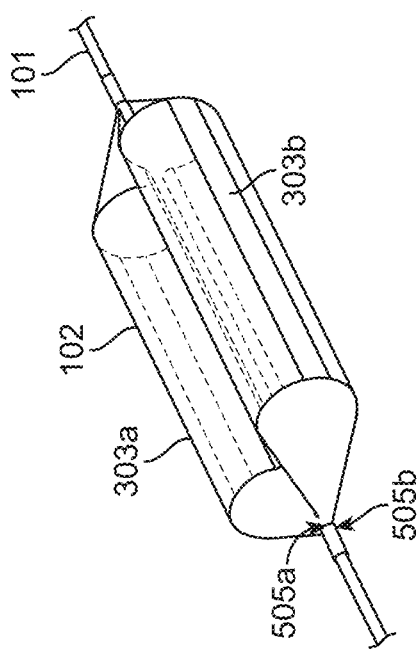

FIGS. 5A-5D show perspective views of the inflatable balloon 102 of FIGS. 4A and 4C. FIG. 5A shows a perspective view of the balloon 102 of FIG. 4A. The inflatable balloon 102 may comprise a cylindrical balloon disposed coaxially about a catheter 101. FIG. 5B shows a cross-section of the balloon 102 of FIG. 5A. FIG. 5C shows a perspective view of the balloon 102 of FIG. 4C having first balloon chamber 303a and second balloon chamber 303b. The first and second balloon chambers 303a, 303b may be generated by forming first and second longitudinal bonds 505a, 505b as described herein. FIG. 5D shows a cross-section of the balloon of FIG. 5C.

In some embodiments, the first balloon chamber 303a and the second balloon chamber 303b may be in fluid communication with one another. In some embodiments, the first balloon chamber 303a and the second balloon chamber 303b may be configured to inflate simultaneously.

In some embodiments, the first balloon chamber 303a and the second balloon chamber 303b may be fluidly independent of one another.

In some embodiments, the first longitudinal bond 505a may extend a length of the inflatable balloon 102 within a range of about 80% to about 99% of the length of the inflatable balloon 102. The first longitudinal bond 505a may, for example, extend 90% of the length of the inflatable balloon 102.

In some embodiments, the second longitudinal bond 505b may extend a length of the inflatable balloon within a range of about 80% to about 99% of the length of the inflatable balloon 102. The second longitudinal bond 505a may, for example, extend 90% of the length of the inflatable balloon 102.

In some embodiments, one or more of the first and second longitudinal bonds 505a, 505b may extend less than the entire length of the inflatable balloon 102 (e.g., less than 100% of the length of the inflatable balloon) such that the first and second balloon chambers 303a, 303b are in fluid communication with one another.

In some embodiments, the portion of the inflatable balloon 102 which is not bonded to the catheter 101, for example, a portion of the inflatable balloon 102 near a proximal and/or distal end of the balloon 102, may have a cylindrical cross-section. In some instances, a fluid outlet port may be disposed in the non-bonded section(s) in order to facilitate simultaneous filling of the first and second balloon chambers 303a, 303b.

In some embodiments, the distal and/or proximal end of the balloon 102 may be bonded to the catheter 101 with a first longitudinal bond but not a second longitudinal bond. The portion of the inflatable balloon 102 which is bonded to the catheter 101 only once may have a heart-shaped cross-section. In some instances, a fluid outlet port may be disposed in the single-bonded section(s) in order to facilitate simultaneous filling of the first and second balloon chambers 303a, 303b.

Figure 6D:
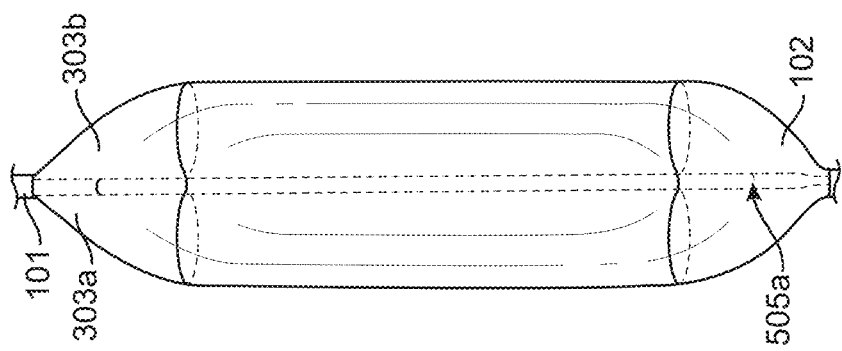
FIGS. 6A-6D show different views of a balloon catheter device having two ellipsoidal balloon chambers, formed using the method described in FIGS. 4A-4C, in the expanded configuration, according to many embodiments.
Figure 6C:
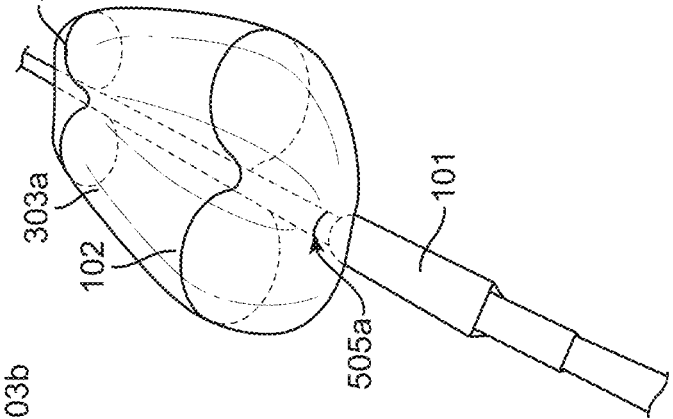
Figure 6B:
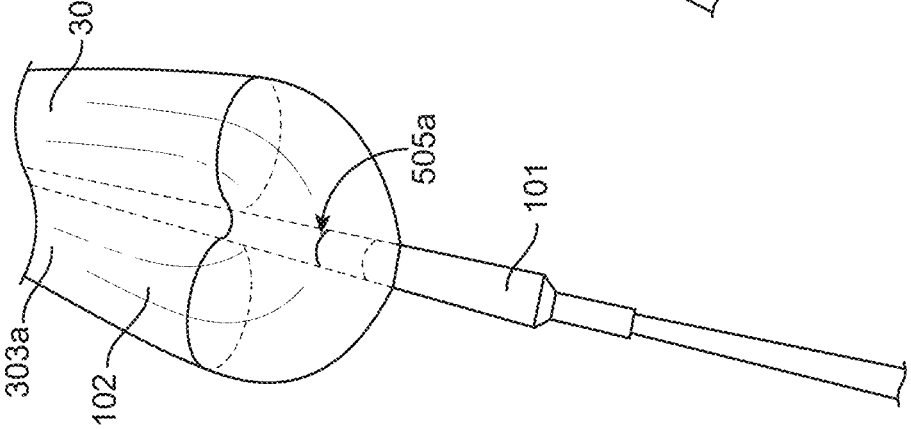
Figure 6A:
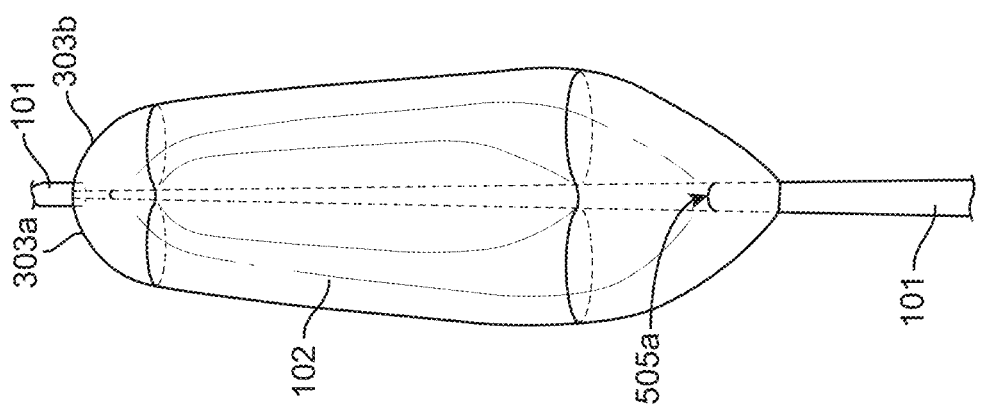

FIGS. 6A-6D show different views of a balloon catheter device 100 having two ellipsoidal balloon chambers 303a, 303b, formed from a conventional barrel balloon catheter using the method described in FIGS. 4A-4C, in the expanded configuration. FIG. 6A shows a top view of the device. FIGS. 6B and 6C show perspective views of the device 100 from different angles. FIG. 6D shows a bottom view of the device 100. The balloon 102 may, for example, comprise a low durometer urethane bonded to the catheter 101 along about 60 mm of the about 70 mm body of the balloon.

Figure 7C:
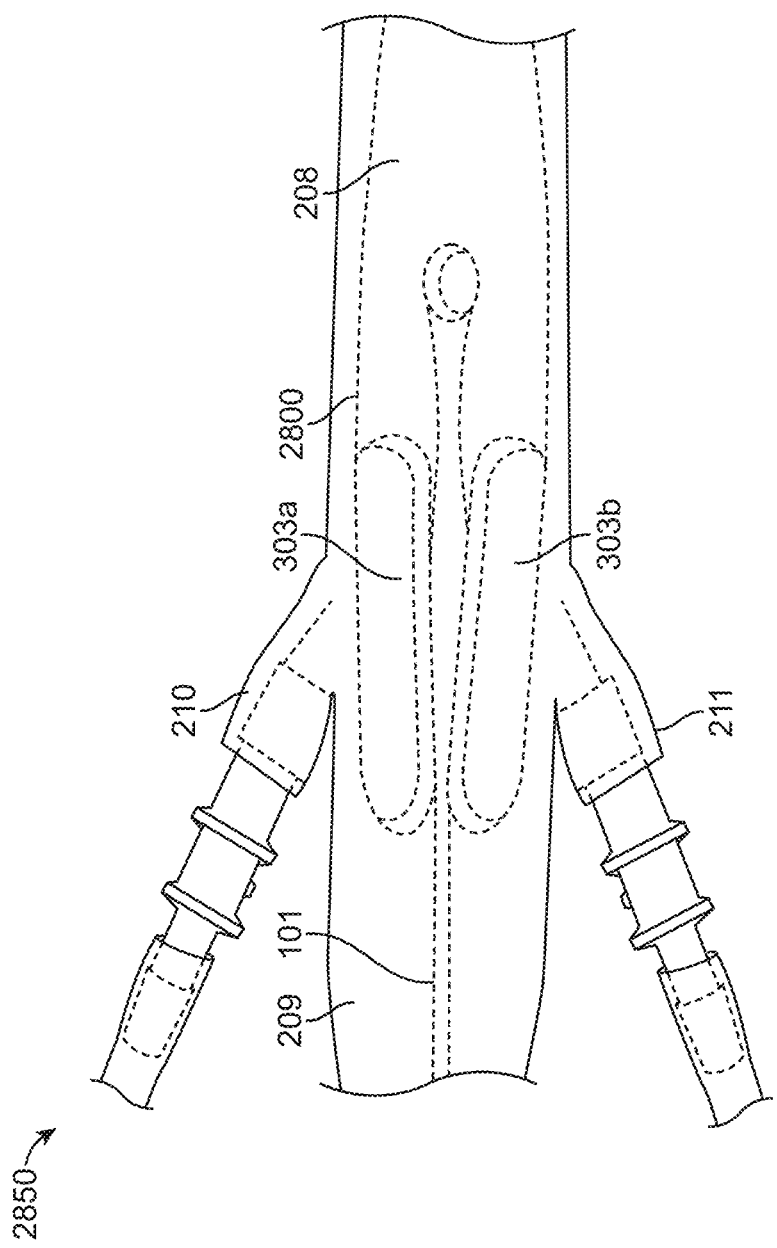

FIGS. 7A-7C show a catheter device 2800 that may comprise a catheter 101 with an inflatable balloon 102 disposed on a proximal portion thereof. The inflatable balloon 102 may comprise a first balloon chamber 303a disposed on a first lateral side of the proximal portion of the catheter 101. The inflatable balloon 102 may comprise a second balloon chamber 303b disposed on a second lateral side of the proximal portion of the catheter 101, for example, opposite the first balloon chamber 303a.

FIG. 7A shows a balloon catheter device 2800 having two ellipsoidal balloon chambers 303a and 303b of an expandable balloon 102 in a collapsed configuration. Device 2800 may be substantially similar to device 100 described herein. FIG. 7B shows the device 2800 in an expanded configuration. The first and second balloon chambers 303a, 303b may, for example, be ellipsoidal as shown. The balloon chambers 303a, 303b may form a dumb-bell or butterfly-like shape about the catheter 101 in cross-section when expanded from the collapsed configuration (FIG. 7A) to the expanded configuration (FIG. 7B). The balloon chambers 303a, 303b may be shaped so as to occlude the left and right renal arteries when expanded while allowing blood to flow between the balloon chambers 303a, 303b along the catheter shaft 101. As described herein, the balloon chambers 303a, 303b may be formed from a single balloon disposed about the catheter 101. As discussed further below, a position indication feature 2900 may be disposed on the surfaces of the balloon chambers 303a, 303b to facilitate the determination of the position and/or orientation of the balloon chambers 303a, 303b and/or whether the renal artery ostia are occluded as described herein. As shown in FIGS. 7A and 7B, the position indication feature 2900 may comprise a plurality of longitudinal radio-opaque markers and/or a radio-opaque marker 2900a disposed on the catheter 101 between the balloon chambers 303a, 303b.

FIG. 7C shows the device 2800 in the expanded configuration inside a model abdominal aorta 2850. The catheter balloon device 2800 is shown positioned within a model abdominal aorta 2850. Generally, the one or more balloon chambers 303a, 303b may be positioned adjacent the orifices of the right renal artery 210 and the left renal artery 211, for example, spanning between the supra-renal aorta 208 and the infra-renal aorta 209, thereby controlling blood flow to any of the right renal artery 210, left renal artery 211, and/or infra-renal aorta 209. While occluding the renal arteries 210, 211, the balloon chambers 303a, 303b may not completely occlude the aorta 2850 and may allow blood flow through the gaps between the balloon chambers 303a, 303b and the catheter 101. In cross-section, the expanded balloon chambers 303a, 303b may assume a dumbbell or butterfly shape, for example, as described herein. The inflatable balloon 102 may be deployed prior to or simultaneously with injection of a contrast agent into the abdominal aorta 2850 of a patient so as to prevent the contrast agent from entering the renal arteries 210, 211. After the bolus of contrast agent has been introduced, the inflatable balloon 102 may be collapsed to allow blood flow to the renal arteries to resume.

Generally, the balloon chambers 303a, 303b may be of any size and/or shape. In particular the size and/or shape may be selected to control the amount of occlusion for each of the left and right arteries. For example, the renal arteries may be located at different distances down the length of the aorta (e.g., viewing the aorta along the coronal plane, the left and right renal arteries may branch away from the aorta at different distances from the aortic arch). In such instances, it may be beneficial to employ balloon chambers that are ellipsoidal (e.g., greater in length along a longitudinal direction of the aorta than in diameter), thereby capable of occluding both the left and right renal artery upon being placed in the initial position. In some instances, the renal arteries may branch at different angles (as viewed along the axial plane) from the aorta between subjects or groups of subjects. In such instances, it may be beneficial to employ balloon chambers which are positioned to match the branching architecture of the patient or group of patients (e.g., balloon chambers which are positioned opposite one another on the catheter for patients with branching opposite one another or balloon chambers which are position less than 180° apart about the catheter for patients with branching less than 180° apart). In some instances, it may be beneficial to employ balloon chambers shaped to deform when contacting the aorta and "spread" along the wall in order to occlude a typical range of angles for a particular group of subjects. In some instances it may be beneficial to employ balloon chambers sized or shaped to occlude a typical range of angles for a particular group of subjects. The typical range of angles may vary from subject group (e.g., patient population) to subject group and the spread, angle, size, and/or shape of the balloon chambers may be configured to perform for a particular subject group based on the typical range of branching angles. In some embodiments, the size and/or shape of the expandable balloon may be specific for a particular group of subjects. For example, younger subjects (e.g., under 15 years of age) may require balloon chambers that are shorter in length and/or width (e.g., in an un-inflated state) as compared to adults (e.g., 15 years of age and older). In another example, balloon chambers of a particular size and/or shape may be suitable for subjects originating from a given geographical location or ethnic background due to genetic and physiological variations between subjects or groups of subjects (e.g., Asians vs. Caucasians). Non-limiting examples of balloon length include about 1 millimeter (mm), about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, about 40 mm, 41 mm, about 42 mm, about 43 mm, about 44 mm, about 45 mm, about 46 mm, about 47 mm, about 48 mm, about 49 mm, about 50 mm, about 60 mm, about 70 mm, about 80 mm, about 90 mm, about 100 mm, or greater than about 100 mm. Non-limiting examples of balloon diameter include about 1 millimeter (mm), about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, about 40 mm, 41 mm, about 42 mm, about 43 mm, about 44 mm, about 45 mm, about 46 mm, about 47 mm, about 48 mm, about 49 mm, about 50 mm, about 60 mm, about 70 mm, about 80 mm, about 90 mm, about 100 mm, or greater than about 100 mm. In some embodiments, the diameter of the balloon (or one or more balloon chambers) may change from a proximal end of the balloon to a distal end of the balloon. For example, the balloon (or one or more balloon chambers) may be cigar-shaped, torpedo-shaped, or submarine-shaped. The balloon may be any shape suitable for occluding one or more arteries (e.g., renal arteries). Non-limiting examples of balloon shapes include spherical, ellipsoidal, cylindrical, an n-sided prism (pentagonal or hexagonal), where n is any number, conical, and pyramidal.

In some embodiments, one or more balloons or balloon chambers of the device may be inflatable. Inflation of the balloon may expand the balloon to occlude the artery. In some embodiments having two or more balloon chambers, the balloon chambers may be fluidly-connected, and may be inflated together. In other embodiments, the balloon chambers may not be fluidly connected, and may be capable of independently inflating. In some embodiments, the balloon chambers may be fluidly connected, wherein a fluid connection may be opened or closed as needed, thereby allowing inflation of two or more balloon chambers together or inflation of each balloon chamber separately. Any number of balloon chambers may be used. A device of the present disclosure may have a single balloon chamber. A device of the present disclosure may have two or more balloon chambers. Non-limiting examples of a multi-chambered balloon device include a device comprising 2 balloon chambers, 3 balloon chambers, 4 balloon chambers, 5 balloon chambers, 6 balloon chambers, 7 balloon chambers, 8 balloon chambers, 9 balloon chambers, 10 balloon chambers, and more than 10 balloon chambers. In some embodiments, one or more balloon chambers of the device may be inflated, and the inflation of the balloon chamber(s) may be synchronized with an injection of a contrast dye (e.g., Urografin) into the subject. In some embodiments, the contrast dye injection may be performed prior to inflating the one or more balloon chambers in the device. In some embodiments, the contrast dye injection may be performed simultaneously with the inflation of the one or more balloon chambers in the device. In some embodiments, the one or more balloon chambers in the device may be inflated prior to or after injection of the contrast dye into the subject.

Figure 8B:
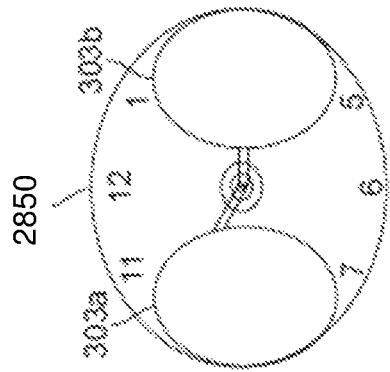
FIGS. 8A-8D show schematics position indication features suitable for use with the balloon catheter devices disclosed herein to determine if the balloon catheter device has occluded the renal arteries, according to many embodiments.
Figure 8A:
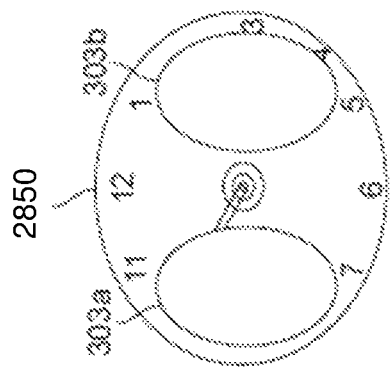
Figure 8D:
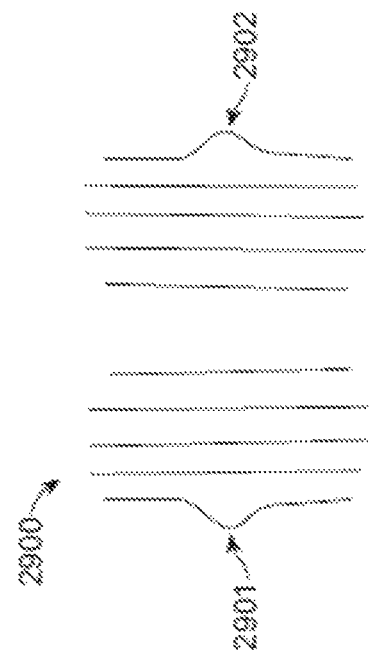
Figure 8C:
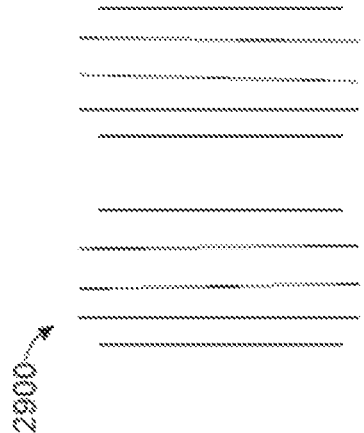

FIGS. 8A-8D show a position indication feature 2900 which can be used to determine if a balloon catheter device occludes the orifices of an artery such as the renal arteries. The renal arteries are not shown for simplicity. FIGS. 8A-8B depict an axial view along the aorta 2850, for example, an abdominal aorta, depicting the relative positions of the first 102 and second 103 catheter balloons in the initial position (FIG. 8A) and the "protective" or inflated position (FIG. 8B). FIGS. 8C and 8D show the position indication feature 2900 in the initial position (FIG. 8C) and the "protected" or expanded position (FIG. 8D). The position indication feature 2900 may be used to help identify the position of the catheter within the abdominal aorta 2850 and/or whether or not the renal arteries have been occluded upon expansion of the balloon chambers 303a, 303b. The position indication feature 2900 may, for example, comprise one or more radio-opaque longitudinal markers as shown. The radio-opaque longitudinal markers may be observed or monitored within the abdominal aorta during positioning of the occlusive element (e.g., the inflatable balloon comprising first and second balloon chambers 303a, 303b) within the abdominal aorta 2850 using x-ray imaging and used to guide positioning of the occlusive element adjacent the renal arteries and/or confirm occlusion of the renal arteries. When unexpanded during positioning (FIGS. 8A, 8C), the radio-opaque longitudinal markers may appear straight within the abdominal aorta 2850. Expansion of the balloon chambers 303a, 303b and occlusion of the renal arteries may be confirmed by the appearance of a bowed section, or "nipple", in the radio-opaque longitudinal markers. FIG. 8D shows "nipples" 2901 and 2902 which may be used as artery (e.g., renal artery) orifice locators. Such "nipples" 2901, 2902 may be formed when the balloon chambers 303a, 303b are expanded and the flexible outer surface of the balloon chambers 303a, 303b curve to partially enter and occlude the left and right renal artery ostia. In the initial, unexpanded configuration (FIGS. 8A and 8C), the radio-opaque longitudinal markers 2900 are straight; and in the protective, expanded position (FIG. 8B and 8D), the outer most radio-opaque longitudinal markers 2900 are curved outwardly at the renal arteria ostia.

Alternatively or in combination, at least a portion of the catheter 101, first balloon chamber 303a, second balloon chamber 303b, or any combination thereof may comprise a radio-opaque material or radio-opaque marker thereon as described herein. Alternatively or in combination, one or more of the balloon chambers may have a radio-opaque material or radio-opaque marker coupled to (e.g., fixedly attached, painted on, etc.) the surface or interior of the one or more balloon chambers. Alternatively or in combination, one or more of the balloon chambers may be inflated with a radio-opaque material as described herein. Similar bowing (e.g., "nipple" formation) may be observed with a balloon made of, coupled to, or inflated with a radio-opaque material, for example.

Figure 9:
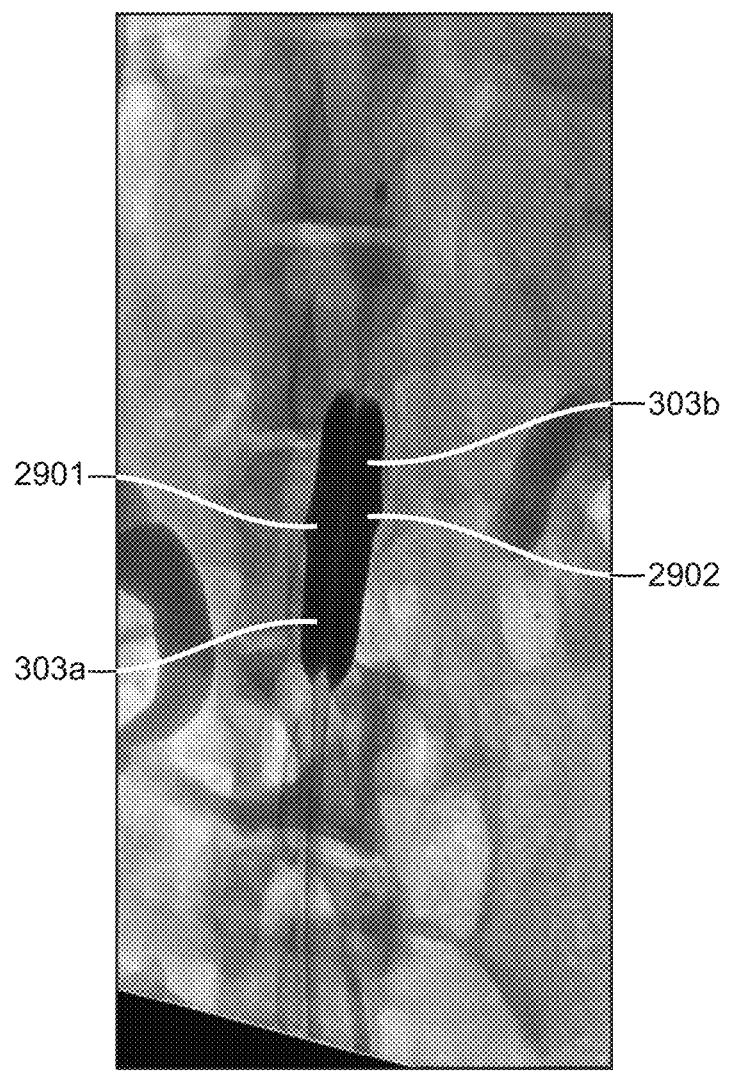
FIG. 9 shows an X-Ray image of the balloon catheter of FIGS. 7A-7C inserted into a subject, with the balloon chambers in the "protective" position.

FIG. 9 shows an X-Ray image of the device 2800 of FIGS. 7A-7C comprising a first balloon chamber 303a and a second balloon chamber 303b inserted into a subject, with the balloon chambers 303a, 303b expanded to be in the "protective" or occlusive position. Arrows identify "nipples" 2901 and 2902 which indicated that the expanded balloon chambers 303a, 303b have occluded the renal arteries as described herein. For example, the balloon chambers 303a, 303b may be inflated with a radiopaque fluid such that the formation of the "nipples" 2901 and 2902 are visible in X-Ray. In cases where the balloon chambers 303a, 303b are expanded with a non-radiopaque fluid such as carbon dioxide or saline, the formation of the "nipples" 2901 and 2902 may be indicated by observing the shape of radio-opaque longitudinal markers, such as those described in FIGS. 8C-8D and FIGS. 10A-13B, on the surface of the balloon chambers 303a, 303b.

Figure 10A:
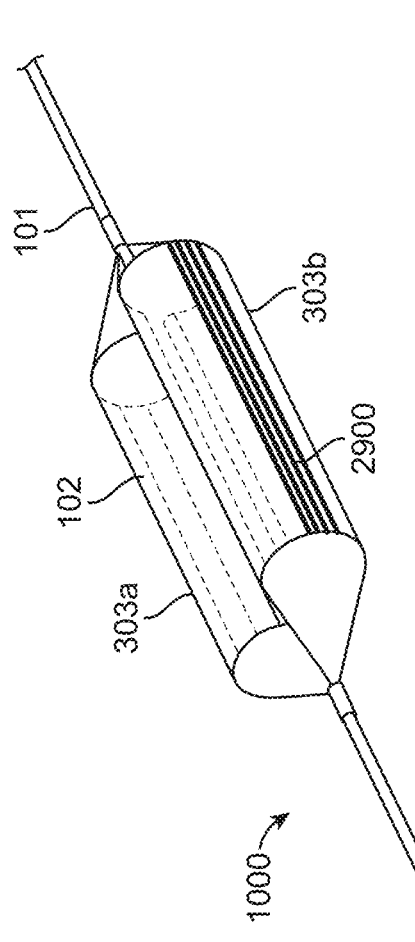
FIGS. 10A-10C show a balloon catheter having longitudinal position indication features which can be used to determine the orientation of the balloon and if the balloon catheter occludes the renal arteries, according to many embodiments.
Figure 10B:
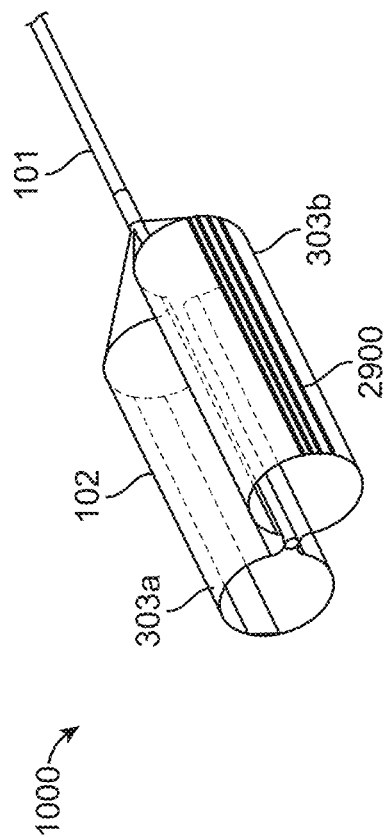
Figure 10C:
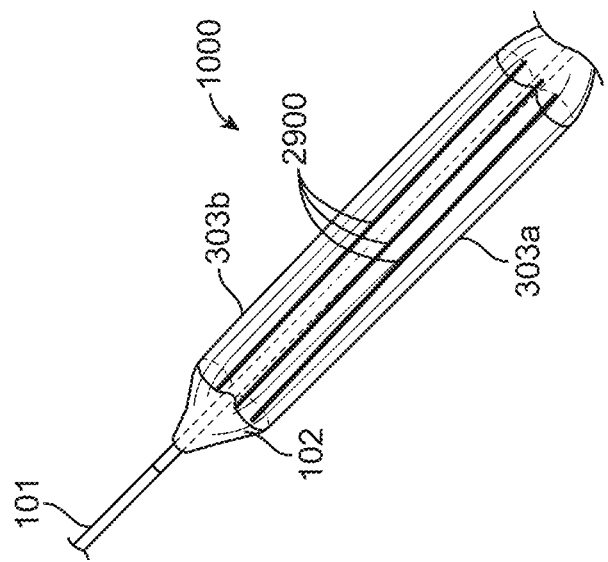

FIGS. 10A-10C show a balloon catheter device 1000 having longitudinal position indication features 2900 which can be used to determine the orientation of the balloon and if the balloon catheter occludes the renal arteries. FIG. 10A shows a perspective view of a balloon 102 having two balloon chambers 303a, 303b with a butterfly-like or figure-eight shaped cross-section about the catheter 101 and having a plurality of longitudinal position indication features 2900 extending thereon. FIG. 10B shows a cross-section perspective view of the balloon of FIG. 10A. FIG. 10C also shows the balloon of FIGS. 10A-10B. The balloon 102 may, for example, comprise three longitudinal position indication features 2900 painted on an external portion of each of the balloon chambers 303a, 303b. The longitudinal position indication features 2900 may, for example, comprise radio-opaque longitudinal markers as described herein. The balloon 102 may, for example, comprise a very low durometer urethane. The radio-opaque longitudinal markers may, for example, comprise a radio-opaque ink which is painted or otherwise applied to the balloon 102. The radio-opaque ink may, for example, comprise a silver-based radio-opaque material.

FIGS. 11A-11B show the deployment of the device 1000 of FIGS. 10A-10C, with the balloon chambers in the "protective" position inside the aorta 2850. The device 1000 may be guided to a desired location within the abdominal aorta 2850 by monitoring a position indication means 2900, for example, three radio-opaque longitudinal markers. FIG. 11A shows a cross-section view of the balloon catheter device of FIGS. 10A-10C deployed in an aorta, with the balloon chambers in the "protective" position with the balloon chambers 303a, 303b positioned to occlude the orifices of the renal arteries 210, 211. FIG. 11B shows a lateral view of the balloon catheter device of FIGS. 10A-10C deployed in an aorta, with the balloon chambers in the "protective" position. The radio-opaque longitudinal markers 2900 may be used to help identify the position of the catheter device 1000 within the abdominal aorta 2850 and/or whether or not the renal arteries 210, 211 have been occluded upon expansion of the balloon chambers 303a, 303b. The radio-opaque longitudinal markers 2900 may be observed or monitored within the abdominal aorta 2850 during positioning of the inflatable balloon 102 comprising first and second balloon chambers 303a, 303b within the abdominal aorta 2850 using x-ray imaging and used to guide positioning of the inflatable balloon 102 adjacent the renal arteries 210, 211 and/or confirm occlusion of the renal arteries 210, 211. When unexpanded during positioning (FIGS. 10A-10C), the radio-opaque longitudinal markers may appear straight within the abdominal aorta 2850. Expansion of the balloon chambers 303a, 303b and occlusion of the renal arteries 210, 211 may confirmed by the appearance of a bowed section, or "nipple", in the radio-opaque longitudinal markers. FIG. 11B shows "nipples" 2901 and 2902 which may be used as artery (e.g., renal artery) orifice locators. Such "nipples" 2901, 2902 may be formed when the balloon chambers 303a, 303b are expanded and the flexible outer surface of the balloon chambers 303a, 303b curve to partially enter and occlude the left and right renal artery 210, 211 ostia. The "nipples" 2901, 2902 may form in part due to lower pressure in the renal arteries 210, 211 compared to the aorta 2850. In the initial, unexpanded configuration (FIGS. 10A-10C), the radio-opaque longitudinal markers 2900 are straight; and in the protective, expanded position (FIGS. 11A-11B), the radio-opaque longitudinal markers 2900 are curved outwardly at the renal arteria 210, 211 ostia.

Figure 12:
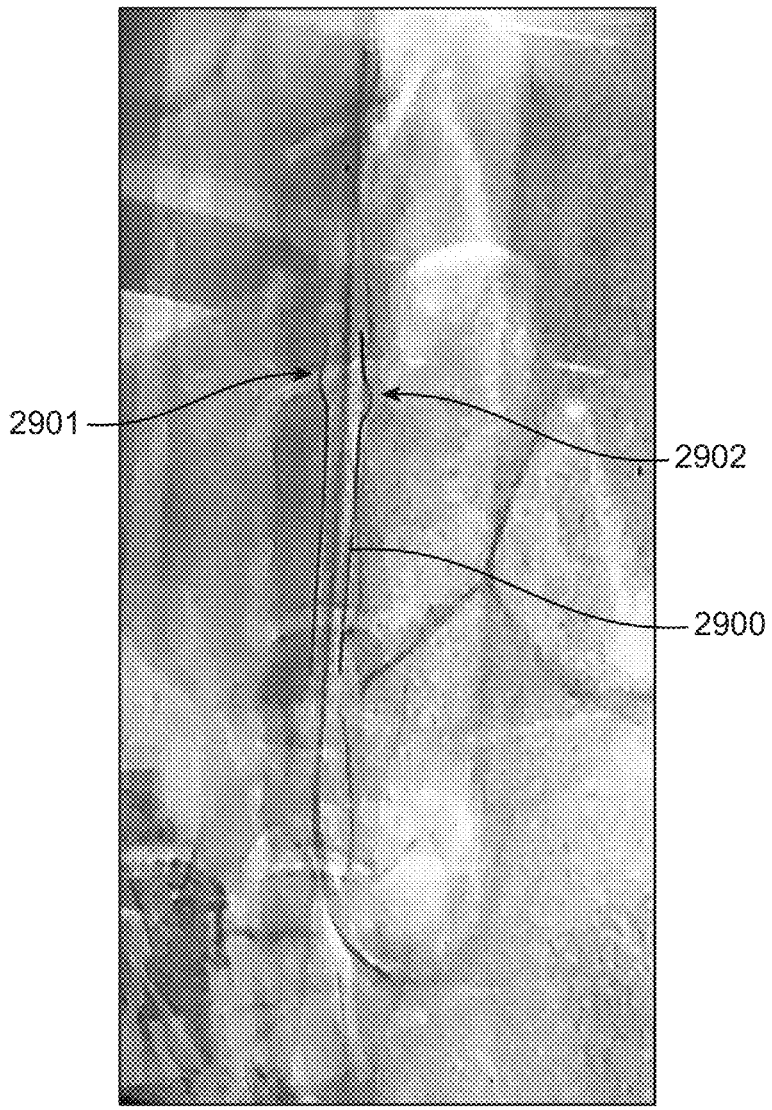
FIG. 12 shows an X-Ray image of the balloon catheter of FIG. 10C inserted into a subject, with the balloon chambers in the "protective" position.
Figure 13:
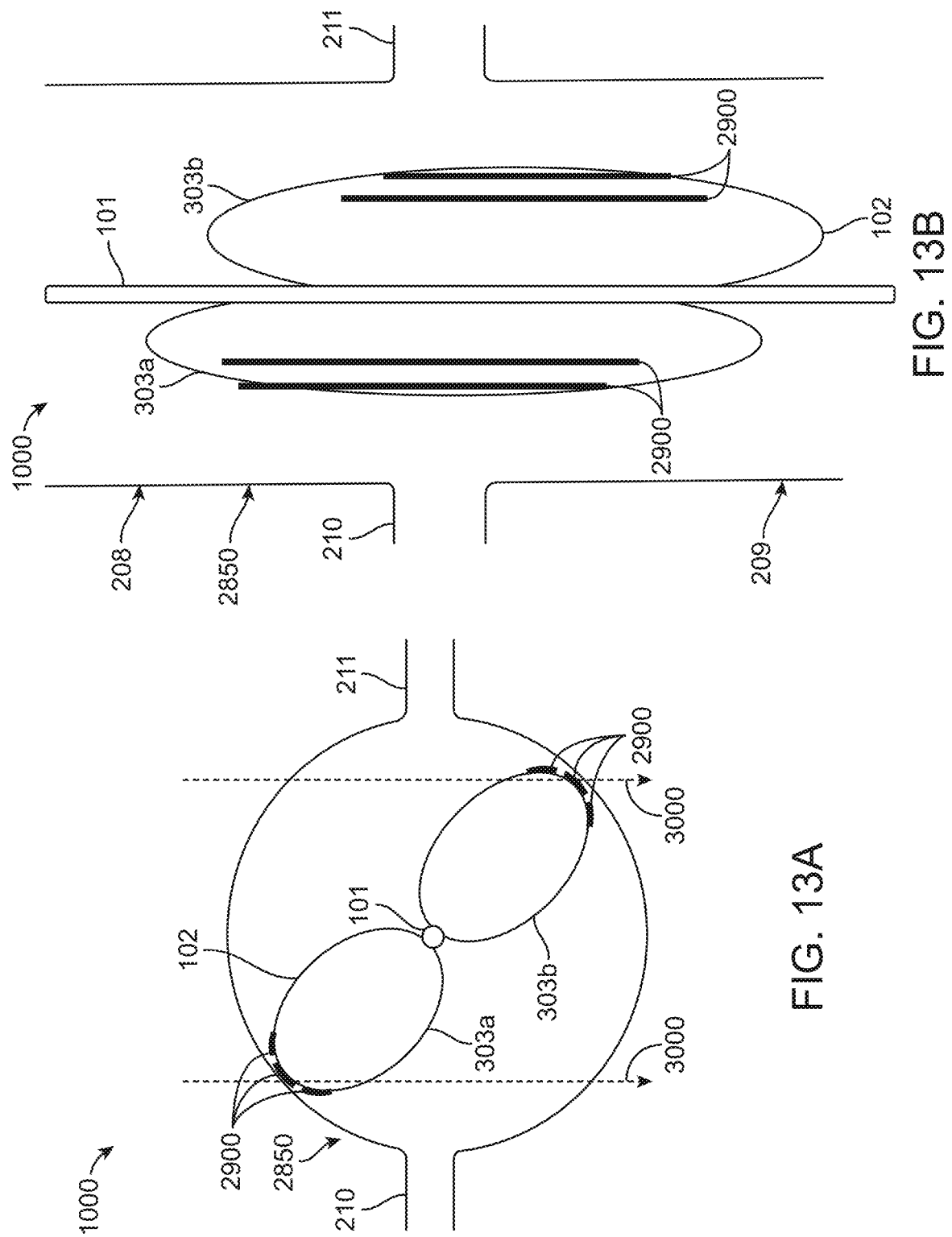
FIGS. 13A-13B show the deployment of the balloon catheter of FIGS. 10A-10C, with the balloon chambers malpositioned inside the aorta, according to many embodiments.

FIG. 12 shows an X-Ray of the balloon catheter of FIG. 10C inserted into a subject, with the balloon chambers in the "protective" position. Arrows identify "nipples" 2901 and 2902 in the radio-opaque longitudinal markers 2900 which indicated that the expanded balloon chambers 303a, 303b have occluded the renal arteries as described herein. For example, the balloon chambers 303a, 303b may be inflated with a non-radiopaque fluid (e.g., carbon dioxide or saline) such that the formation of the "nipples" 2901 and 2902 by the radio-opaque longitudinal markers 2900 on the surface of the balloon chambers 303a, 303b are visible in X-Ray.

FIGS. 13A-13B show the deployment of the embodiment of FIGS. 10A-10C, with the balloon chambers 303a, 303b malpositioned inside the aorta 2850. FIG. 13A shows a cross-section view of the balloon catheter device 1000 of FIGS. 10A-10C deployed in an aorta, with the balloon chambers 303a, 303b malpositioned. FIG. 13B shows a lateral view of the balloon catheter device 1000 deployed in an aorta 2850, with the balloon chambers 303a, 303b malpositioned such that the renal artery 210, 211 ostia are not occluded upon inflation of the balloon 102. As described herein, the radio-opaque longitudinal markers 2900 may be used to help identify the position of the catheter device 1000 within the abdominal aorta 2850 and/or whether or not the renal arteries 210, 211 have been occluded upon expansion of the balloon chambers 303a, 303b. When unexpanded during positioning (FIGS. 10A-10C), the radio-opaque longitudinal markers may appear straight within the abdominal aorta 2850 as described herein. Proper positioning of the balloon 102 in the aorta 2850 may result in the appearance of "nipples" in the radio-opaque longitudinal markers 2900 when expanded, as shown in FIGS. 11A-11B. When malpositioned, as shown in FIGS. 13A-13B, the "nipples" may not be visibly apparent. A lack of "nipples" in the radio-opaque longitudinal markers 2900 may indicate to the user (e.g., a physician) that the balloon 102 should be deflated and re-positioned with aorta 2850 before further procedures are performed (such as contrast agent injection as described herein).

The radio-opaque longitudinal markers 2900 may also be used to determine the orientation of the device 1000 inside the abdominal aorta 2850 (or other blood vessel of interest to one of ordinary skill in the art). The radio-opaque longitudinal markers 2900 may be configured to indicate the orientation of the inflatable balloon 102, in this example the first and second balloon chambers 303a, 303b, when positioned adjacent renal artery 210, 211 ostia of the subject. The orientation of the balloon 102 (and balloon chambers 303a, 303b) may be important in the case where the balloon 102 is malpositioned between the renal arteries 210, 211 ostia such that the ostia are not occluded as shown in FIGS. 13A-13B. The three radio-opaque longitudinal markers 2900 shown in FIGS. 11A-11B may be positioned on each of the balloon chambers 303a, 303b such that, when properly positioned in the "protective" position to occlude the ostia, the radio-opaqueness of each of the three markers 2900 is summed in the plane of the x-ray (taken along the lines 3000) shown in FIG. 11A, giving the appearance of very visible, dense line(s) under x-ray. When malpositioned as shown in FIG. 13A, the lines may not be summed and may therefore be less visible in the x-ray. Therefore, the density (e.g., visibility) of the lines under x-ray may inform the user as to the orientation of the balloon 102 (and balloon chambers 303a, 303b).

Any of the devices described herein may further comprise a time-delayed release mechanism configured to automatically collapse the inflatable balloon after a pre-determined amount of time following deployment (i.e., inflation). The time-delayed release mechanism may be provided on a handle or controller of the device.

For example, the catheter shaft device 100, 1000, or 2800 may further comprise a time-delayed release mechanism configured to automatically collapse the expandable mesh braid after a pre-determined amount of time following deployment. The time-delayed release mechanism may, for example, comprise an energy accumulation and storage component and a time-delay component. For example, the time-delayed release mechanism may comprise a spring with a frictional damper, an example of which is described in FIG. 14. The energy accumulation and storage component may, for example, be a spring or spring-coil or the like. The time-delayed release mechanism may, for example, be adjustable by one or more of the user, the manufacturer, or both. The time-delayed release mechanism may further comprise a synchronization component to synchronize the injection of a contrast media or other harmful agent with the opening or closing of the catheter shaft device. For example, injection may be synchronized with occlusion of the renal arteries by the expandable mesh braid such that a contrast media may be prevented from entering the renal arteries.

Figure 14:
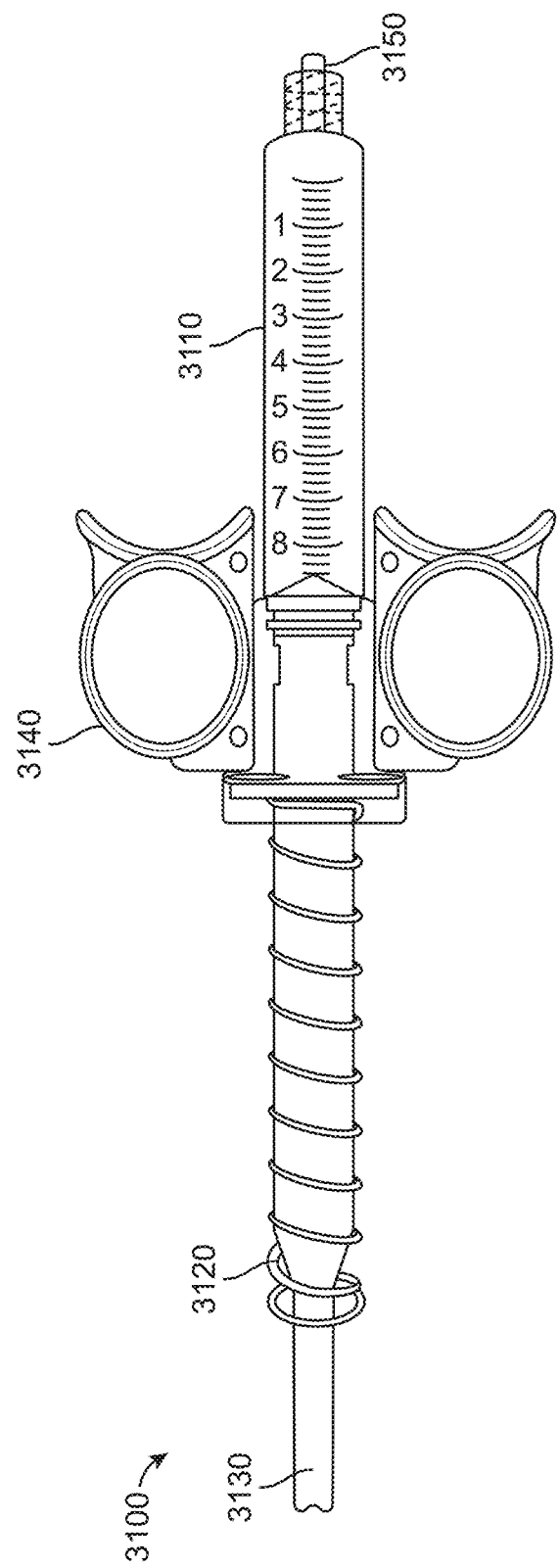
FIG. 14 shows an exemplary time-delayed release mechanism suitable for use with the balloon catheters disclosed herein, according to many embodiments; the time-delayed release mechanism may be configured to automatically collapse the inflatable balloon after a pre-determined amount of time following deployment.

FIG. 14 shows an embodiment of a time-delayed release mechanism 3100 configured to automatically collapse the inflatable balloon after a pre-determined amount of time following deployment. Any of the devices described herein may further comprise a time-delayed release mechanism

3100. The time-delayed release mechanism 3100 may be configured to facilitate expansion and subsequent collapse any of the expandable occlusive elements described herein after a pre-determined amount of time following deployment or expansion of the occlusive element (e.g., inflatable balloon). For example, the time-delayed release mechanism 3100 may be used to automatically deflate an inflatable balloon after a pre-determined amount of time. The time-delayed release mechanism may, for example, comprise an energy accumulation and storage component and a time-delay component. For example, the time-delayed release mechanism may comprise a spring with a frictional damper. The energy accumulation and storage component may, for example, be a spring or spring-coil or the like. The time-delayed release mechanism 3100 may, for example, comprise a syringe 3110 and a spring 3120 disposed around a syringe pump 3130. The tip 3150 of the syringe 3110 may be configured to attach to the distal end of the catheter device (not shown), for example, via a press-fit, screw-fit, or luer-lock connector. The release mechanism 3100 may further comprise a handle 3140 which the user may grip while depressing the syringe pump 3130 and attached spring 3120 into the syringe 3110 to expand the inflatable balloon (not shown). Actuation of the syringe pump 3130 may, in the case of a balloon catheter, for example, force a fluid (e.g., liquid or gas) into the balloon(s) via the tip connection 3150 to the catheter device in order to inflate and expand the balloon (e.g., expand one or more of the balloon chambers) to an expanded configuration. Removal of the pressure applied to the syringe pump 3130 may cause the spring 3120 to release the energy it accumulated by being depressed and quickly retract the syringe pump 3130 from its depressed position within the syringe 3110 to deflate and collapse the balloon after a pre-determined amount of time. The time-delayed release mechanism 3120 may further comprise a frictional damper configured to introduce the pre-determined amount of time between the inflation of the balloon, release of the syringe pump 3130, and the release of energy by the spring 3120. It will be understood by one of ordinary skill in the art that the amount of friction applied by the damper to the syringe pump 3130 and/or spring 3120 may be calibrated to generate any pre-determined time-delay desired such as by providing the spring 3120 with various spring constants depending on the time-delay desired.

The time-delayed release mechanism 3100 may, for example, be adjustable by one or more of the user, the manufacturer, or both. The time-delayed release mechanism 3100 may further comprise a synchronization component to synchronize the injection of a contrast media or other harmful agent with the opening or closing of the balloon catheter shaft device as described herein. For example, injection may be synchronized with occlusion of the renal arteries by the first and second balloon chambers such that a contrast media may be prevented from entering the renal arteries.

Figure 15:
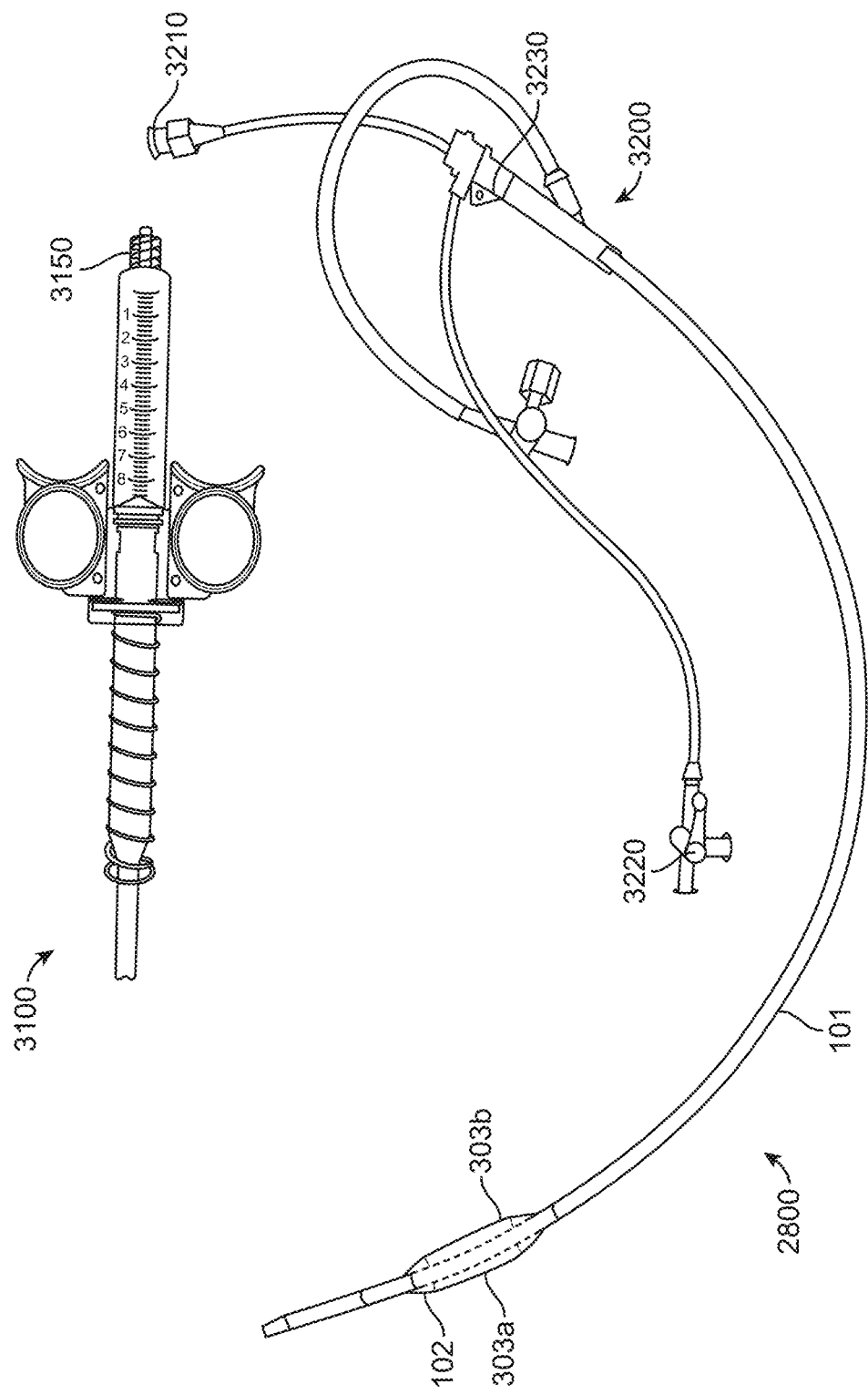
FIG. 15 shows a perspective view of a balloon catheter system, including the balloon catheter of FIGS. 7A-7C and the time-delayed release mechanism of FIG. 14, according to many embodiments.

FIG. 15 shows a further embodiment of the present disclosure including the catheter device 2800 of FIGS. 7A-7C and the time-delayed release mechanism 3100 of FIG. 14. The catheter device 2800 may comprise a catheter 101 with a first balloon chamber 303*a* and a second balloon chamber 303*b* on a proximal portion thereof as described herein. A distal portion 3200 of the catheter 101 may comprise a connection element 3210 configured to connect to the tip 3150 of the time-delayed release mechanism 3100. The distal portion 3200 of the catheter 101 may be configured to remain external to the subject when the first and second balloon chambers 303*a*, 303*b* are positioned adjacent the renal arteries of the subject. The catheter 101 and the syringe 3110 may be fluidly connected, for example, to allow a fluid to pass from the syringe 3110 to the catheter 101 and into the balloon chambers 303*a*, 303*b* via the catheter 101. Actuation of the time-delayed release mechanism 3100 may expand the balloon chambers 303*a*, 303*b* with the fluid as described herein. The distal portion 3200 of the catheter 101 may comprise one or more infusion port 3220 as described herein. The infusion port 3220 may, for example, be configured to infuse a medication or other fluid (e.g., normal saline) into the aorta, for example via a side aperture in the catheter 101 (not shown). The distal portion 3200 of the catheter 101 may further comprise one or more orientation indication feature 3230. The orientation indication feature 3230 may be configured to indicate the orientation of the occlusive element, in this example the first and second balloon chambers 303*a*, 303*b*, when positioned adjacent renal artery ostia of the subject. The orientation indication feature 3230 may, for example, comprise one or more of a visible marking, a protrusion, a wing, a flag, or the like. The orientation indication feature 3230 may be aligned with the first and second balloon chambers 303*a*, 303*b* in a particular manner such that the orientation of the orientation indication feature 3230 outside of the subject may be indicative of the orientation of the first and second balloons 102, 103 inside the subject. For example, the orientation indication feature 3230 may comprise a pair of wings as shown which include a first wing aligned (i.e., facing the same radially outward direction as) with the first balloon chamber 303*a* and a second wing aligned with (i.e., facing the same radially outward direction as) the second balloon chamber 303*b*. The catheter 101 may be sufficiently stiff such the orientation indication feature 3230 maintains alignment with the balloon chambers 303*a*, 303*b* as the catheter 101 is torqued or rotated. For example, the orientation indication feature 3230 may be configured to lie approximately parallel to (or alternatively face perpendicularly away from or towards, or be otherwise oriented in relation to) the ground when the first and second balloon chambers 303*a*, 303*b* are properly positioned within the abdominal aorta adjacent the renal arteries of the subject. Alternatively or in combination, the one or more position indication features may be used to determine the orientation of the balloon chambers 303*a*, 303*b* within the abdominal aorta as described herein. It will be understood by one of ordinary skill in the art that any of the catheter devices described herein may be attached to a time-delayed release mechanism 3100, comprise one or more infusion port 3220, and/or comprise one or more orientation indication feature 3230 in a similar manner as described herein.

Figure 16:
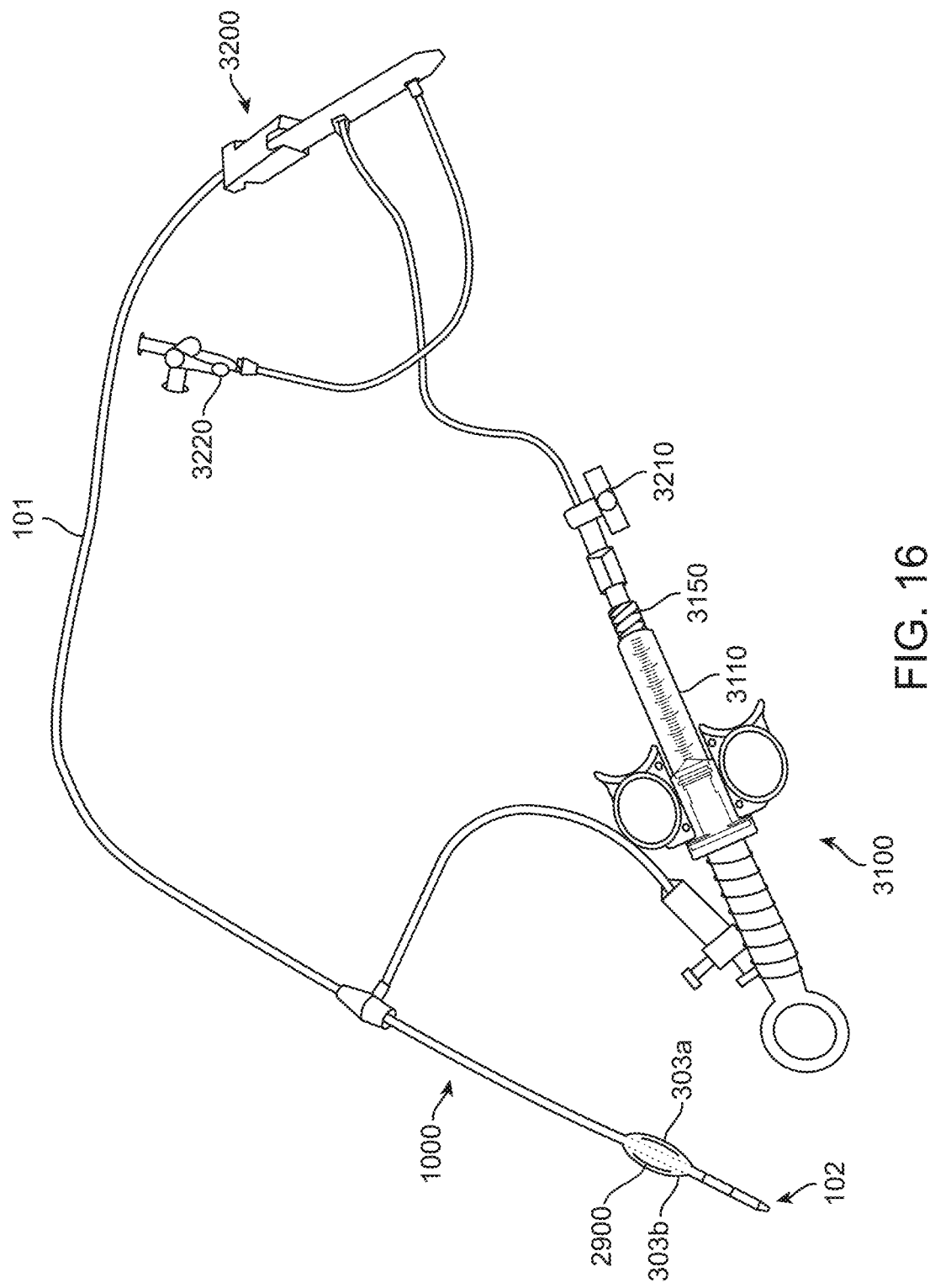
FIG. 16 shows a top view of another balloon catheter system, including the balloon catheter of FIGS. 10A-10C and the time-delayed release mechanism of FIG. 14, according to many embodiments.

FIG. 16 shows another embodiment of the present disclosure including the balloon catheter device 1000 of FIGS. 10A-10C and the time-delayed release mechanism 3100 of FIG. 14. The catheter device 1000 may comprise a catheter 101 with a first balloon chamber 303*a* and a second chamber 303*b* on a proximal portion thereof as described herein. A distal portion 3200 of the catheter 101 may comprise a connection element 3210 configured to connect to the tip 3150 of the time-delayed release mechanism 3100. The distal portion 3200 of the catheter 101 may be configured to remain external to the subject when the first and second balloon chambers 303*a*, 303*b* are positioned to occlude the renal arteries of the subject. The balloon 102 may comprise longitudinal position indication features, or radio-opaque longitudinal markers 2900 painted on an external portion of each of the balloon chambers 303*a* and 303*b*. The radio-opaque longitudinal markers 2900 may be used to help identify the position of the catheter device 1000 within the abdominal aorta and/or whether or not the renal arteries have been occluded upon expansion of the balloon chambers 303a, 303b. The catheter 101 and the syringe 3110 may be fluidly connected, for example, to allow a fluid to pass from the syringe 3110 to the catheter 101 and into the balloon chambers 303a, 303b via the catheter 101. Actuation of the time-delayed release mechanism 3100 may expand the balloon chambers 303a, 303b with the fluid as described herein. The distal portion 3200 of the catheter 101 may comprise one or more infusion port 3220 as described herein. The infusion port 3220 may, for example, be configured to infuse a medication or other fluid (e.g., normal saline) into the aorta, for example via a side aperture in the catheter 101 (not shown). The distal portion 3200 of the catheter 101 may further comprise one or more orientation indication feature 3230. The orientation indication feature 3230 may be configured to indicate the orientation of the occlusive element, in this example the first and second balloon chambers 303a, 303b, when positioned to occlude the orifices of the renal arteries of the subject. The orientation indication feature 3230 may, for example, comprise one or more of a visible marking, a protrusion, a wing, a flag, or the like. The orientation indication feature 3230 may be aligned with the first and second balloon chambers 303a, 303b in a particular manner such that the orientation of the orientation indication feature 3230 outside of the subject may be indicative of the orientation of the balloon 102 inside the subject. For example, the orientation indication feature 3230 may comprise a pair of wings as shown which include a first wing aligned (i.e., facing the same radially outward direction as) with the first balloon chamber 303a and a second wing aligned with (i.e., facing the same radially outward direction as) the second balloon chamber 303b. The catheter 101 may be sufficiently stiff such the orientation indication feature 3230 maintains alignment with the balloon chambers 303a, 303b as the catheter 101 is torqued or rotated. For example, the orientation indication feature 3230 may be configured to lie approximately parallel to (or alternatively face perpendicularly away from or towards, or be otherwise oriented in relation to) the ground when the first and second balloon chambers 303a, 303b are properly positioned to occlude the orifices of the renal arteries of the subject. Alternatively or in combination, the one or more position indication features may be used to determine the orientation of the balloon chambers 303a, 303b within the abdominal aorta as described herein. It will be understood by one of ordinary skill in the art that any of the catheter devices described herein may be attached to a time-delayed release mechanism 3100, comprise one or more infusion port 3220, and/or comprise one or more orientation indication feature 3230 in a similar manner as described herein.

While preferred embodiments of the present disclosure have been shown and described herein, it will be obvious to those skilled in the art that such embodiments are provided by way of example only. Numerous variations, changes, and substitutions will now occur to those skilled in the art without departing from the scope of the present disclosure. It should be understood that various alternatives to the embodiments described herein may be employed in practicing the inventions of the present disclosure. It is intended that the following claims define the scope of the invention and that methods and structures within the scope of these claims and their equivalents be covered thereby.

What is claimed is:

1. A system for occluding vasculature of a subject, the system comprising:

a catheter shaft comprising a proximal portion and a distal portion;

an inflatable balloon disposed on the proximal portion of the catheter shaft; and a time-delayed release mechanism in communication with the inflatable balloon, wherein the inflatable balloon comprises a first balloon chamber and a second balloon chamber, the first and second balloon chambers being formed by one or more of (i) fixedly attaching a first length of the inflatable balloon to the catheter shaft along a longitudinal axis of the catheter to form a first longitudinal bond extending thereon or (ii) fixedly attaching a second length of the inflatable balloon to the catheter shaft along the longitudinal axis of the catheter to form a second longitudinal bond extending thereon, wherein the first longitudinal bond extends 80% of the length of the inflatable balloon, wherein the inflatable balloon has an expanded configuration which, when advanced into a blood vessel and positioned adjacent blood vessel ostia of the subject, is sized to occlude the blood vessel ostia while allowing blood flow over the catheter shaft, wherein the distal portion is configured to remain outside a body of the subject when the proximal portion is positioned adjacent blood vessel ostia of the subject, and wherein the time-delayed release mechanism is configured to collapse the inflatable balloon after a predetermined amount of time following expansion of the inflatable balloon.

2. The system of claim 1, wherein the first balloon chamber and the second balloon chamber are each longitudinal cylindrical balloon chambers.

3. The system of claim 1, wherein the first balloon chamber and the second balloon chamber are in fluid communication with one another.

4. The system of claim 3, wherein the first balloon chamber and the second balloon chamber are configured to inflate simultaneously.

5. The system of claim 1, wherein the second longitudinal bond extends 90% of the length of the inflatable balloon.

6. The system of claim 1, wherein the inflatable balloon comprises a figure-eight or dumbbell cross section about the catheter shaft disposed therein.

7. The system of claim 1, wherein the time-delayed release mechanism comprises an energy accumulation and storage component.

8. The system of claim 7, wherein the energy accumulation and storage component comprises a spring.

9. The system of claim 8, wherein the energy accumulation and storage component comprises a syringe comprising a plunger, and wherein the spring is coupled to the plunger.

10. The system of claim 1, further comprising one or more position indication features disposed on the expandable balloon.

11. The system of claim 10, wherein the one or more position indication feature comprises one or more radio-opaque markers.

12. The system of claim 11, wherein the one or more radio-opaque markers comprises one or more radio-opaque longitudinal markers.

13. The system of claim 12, wherein the one or more radio-opaque longitudinal markers comprises a plurality of radio-opaque longitudinal markers disposed on the expandable balloon along a longitudinal axis of the expandable balloon.

14. The system of claim 12, wherein the one or more radio-opaque longitudinal markers are configured to indicate the orientation of the expandable balloon when positioned adjacent renal artery ostia of the subject.

15. The system of claim 12, wherein the one or more radio-opaque longitudinal markers are configured to change from a straight configuration to a bowed configuration when expanded adjacent blood vessel ostia of the subject.

16. The system of claim 1, wherein fixedly attaching comprises adhering.

17. The system of claim 1, wherein fixedly attaching comprises bonding.

18. The system of claim 17, wherein bonding comprises adhesive or thermal bonding.

19. The system of claim 1, wherein the system is configured for preventing acute kidney injury from contrast agent introduced into vasculature of the subject.

20. The system of claim 1, wherein the blood vessel is an abdominal aorta and wherein the blood vessel ostia are renal artery ostia.

21. A system for occluding vasculature of a subject, the system comprising:
    a catheter shaft comprising a proximal portion and a distal portion;
    an inflatable balloon disposed on the proximal portion of the catheter shaft; and
    a time-delayed release mechanism in communication with the inflatable balloon,
    wherein the inflatable balloon comprises a first balloon chamber and a second balloon chamber, the first and second balloon chambers being formed by one or more of (i) fixedly attaching a first length of the inflatable balloon to the catheter shaft along a longitudinal axis of the catheter to form a first longitudinal bond extending thereon or (ii) fixedly attaching a second length of the inflatable balloon to the catheter shaft along the longitudinal axis of the catheter to form a second longitudinal bond extending thereon,
    wherein the inflatable balloon has an expanded configuration which, when advanced into a blood vessel and positioned adjacent blood vessel ostia of the subject, is sized to occlude the blood vessel ostia while allowing blood flow over the catheter shaft,
    wherein the distal portion is configured to remain outside a body of the subject when the proximal portion is positioned adjacent blood vessel ostia of the subject,
    wherein the time-delayed release mechanism is configured to collapse the inflatable balloon after a predetermined amount of time following expansion of the inflatable balloon, further comprising:
    one or more position indication features disposed on the expandable balloon, wherein the one or more position indication features comprises one or more radio-opaque longitudinal markers wherein the one or more radio-opaque longitudinal markers are configured to change from a straight configuration to a bowed configuration when the expandable balloon is expanded adjacent blood vessel ostia of the subject.

22. The system of claim 21, wherein the first balloon chamber and the second balloon chamber are each longitudinal cylindrical balloon chambers.

23. The system of claim 21, wherein the first balloon chamber and the second balloon chamber are in fluid communication with one another.

24. The system of claim 23, wherein the first balloon chamber and the second balloon chamber are configured to inflate simultaneously.

25. The system of claim 21, wherein the first longitudinal bond extends 80% of the length of the inflatable balloon.

26. The system of claim 21, wherein the second longitudinal bond extends 90% of the length of the inflatable balloon.

27. The system of claim 21, wherein the inflatable balloon comprises a figure-eight or dumbbell cross section about the catheter shaft disposed therein.

28. The system of claim 21, wherein the time-delayed release mechanism comprises an energy accumulation and storage component.

29. The system of claim 28, wherein the energy accumulation and storage component comprises a spring.

30. The system of claim 29, wherein the energy accumulation and storage component comprises a syringe comprising a plunger, and wherein the spring is coupled to the plunger.

31. The system of claim 21, wherein the one or more radio-opaque longitudinal markers comprises a plurality of radio-opaque longitudinal markers disposed on the expandable balloon along a longitudinal axis of the expandable balloon.

32. The system of claim 21, wherein the one or more radio-opaque longitudinal markers are configured to indicate the orientation of the expandable balloon when positioned adjacent renal artery ostia of the subject.

33. The system of claim 21, wherein fixedly attaching comprises adhering.

34. The system of claim 21, wherein fixedly attaching comprises bonding.

35. The system of claim 34, wherein bonding comprises adhesive or thermal bonding.

36. The system of claim 21, wherein the system is configured for preventing acute kidney injury from contrast agent introduced into vasculature of the subject.

37. The system of claim 21, wherein the blood vessel is an abdominal aorta and wherein the blood vessel ostia are renal artery ostia.

* * * * *